US012714428B2

(12) United States Patent
Shikhman et al.

(10) Patent No.: US 12,714,428 B2
(45) Date of Patent: Aug. 25, 2026

(54) SURGICAL CLIP AND DEPLOYMENT SYSTEM

(71) Applicant: BOSTON SCIENTIFIC SCIMED, INC., Maple Grove, MN (US)

(72) Inventors: Oleg Shikhman, Trumbull, CT (US); Roddi Simpson, Higganum, CT (US); Scott Reed, Winchester, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 383 days.

(21) Appl. No.: 18/286,806

(22) PCT Filed: May 6, 2022

(86) PCT No.: PCT/US2022/027979

§ 371 (c)(1),
(2) Date: Oct. 13, 2023

(87) PCT Pub. No.: WO2022/240661

PCT Pub. Date: Nov. 17, 2022

(65) Prior Publication Data

US 2024/0138836 A1 May 2, 2024

Related U.S. Application Data

(63) Continuation-in-part of application No. 16/772,454, filed as application No. PCT/US2018/067432 on Dec. 23, 2018, now Pat. No. 11,413,050.

(Continued)

(51) Int. Cl.

*A61B 17/08* (2006.01)
*A61B 17/00* (2006.01)

(Continued)

(52) U.S. Cl.

CPC ...... *A61B 17/083* (2013.01); *A61B 17/00234* (2013.01); *A61B 17/1227* (2013.01); *A61B 17/1285* (2013.01); *A61B 2017/00296* (2013.01)

(58) Field of Classification Search

CPC ............ A61B 17/00234; A61B 17/083; A61B 17/12013; A61B 17/1227; A61B 17/1285;

(Continued)

(56) References Cited

U.S. PATENT DOCUMENTS

| | | | | |
|---|---|---|---|---|
| 3,586,002 A * | 6/1971 | Wood | A61B 17/083 | 606/221 |
| 4,217,902 A * | 8/1980 | March | A61B 17/083 | 606/221 |

(Continued)

FOREIGN PATENT DOCUMENTS

| | | |
|---|---|---|
| CN | 111214272 A | 6/2020 |
| KR | 101765648 | 8/2017 |

(Continued)

OTHER PUBLICATIONS

European Search Report 18898852.1 Dated Aug. 19, 2021.

(Continued)

*Primary Examiner* — Ryan J. Severson

(74) *Attorney, Agent, or Firm* — Seager, Tufte & Wickhem, LLP

(57) ABSTRACT

A system for compressing body tissue including a clip having first and second tissue compressing surfaces. The clip is movable from a closed position to an open position wherein the clip receives tissue between the first and second tissue compressing surfaces to compress tissue between the first and second tissue compressing surfaces. A clip deployment device has a first clip engagement member and a second clip engagement member engageable with the clip, (Continued)

the first and second clip engagement members movable between first and second positions to controllably move the clip.

20 Claims, 12 Drawing Sheets

Related U.S. Application Data

(60) Provisional application No. 63/253,227, filed on Oct. 7, 2021, provisional application No. 63/186,887, filed on May 11, 2021, provisional application No. 62/648,586, filed on Mar. 27, 2018, provisional application No. 62/648,593, filed on Mar. 27, 2018, provisional application No. 62/613,902, filed on Jan. 5, 2018.

(51) Int. Cl.
*A61B 17/122* (2006.01)
*A61B 17/128* (2006.01)

(58) Field of Classification Search
CPC ........... A61B 2017/00575; A61B 2017/00584; A61B 2017/00592; A61B 2017/00623; A61B 2017/00929; A61B 2017/12018; A61B 2018/00601; A61B 2018/141
See application file for complete search history.

(56) References Cited

U.S. PATENT DOCUMENTS 4,716,886 A 1/1988 Schulman et al.
4,796,627 A 1/1989 Tucker
4,832,027 A 5/1989 Utz
5,259,366 A 11/1993 Reydel et al.
5,779,720 A 7/1998 Walder-Utz et al.
6,428,548 B1 8/2002 Durgin et al.
6,849,078 B2 2/2005 Durgin et al.
6,911,032 B2 6/2005 Jugenheimer et al.
7,435,251 B2 * 10/2008 Green ................ A61B 17/0487 606/232
7,488,334 B2 2/2009 Jugenheimer et al.
7,727,247 B2 * 6/2010 Kimura .............. A61B 17/1285 606/142
7,806,904 B2 10/2010 Carley et al.
7,815,565 B2 10/2010 Stefanchik et al.
7,879,052 B2 * 2/2011 Adams ................. A61B 17/122 606/157
7,892,244 B2 2/2011 Monassevitch
8,043,307 B2 10/2011 Jugenheimer et al.
8,187,286 B2 5/2012 Jugenheimer et al.
8,192,349 B2 6/2012 Schurr et al.
8,469,995 B2 6/2013 Cummins et al.
8,518,057 B2 8/2013 Walberg et al.
8,685,043 B2 4/2014 Jugenheimer et al.
8,685,048 B2 4/2014 Adams et al.
8,709,027 B2 4/2014 Adams et al.
8,721,528 B2 5/2014 Ho et al.
8,784,436 B2 7/2014 Ho et al.
8,888,792 B2 11/2014 Harris et al.
8,974,371 B2 3/2015 Durgin et al.
9,017,349 B2 4/2015 Privitera et al.
9,055,942 B2 6/2015 Balbierz
9,138,227 B2 9/2015 Schostek et al.
9,149,276 B2 10/2015 Voss
9,215,968 B2 12/2015 Schostek et al.
9,295,470 B2 3/2016 Baur et al.
9,370,369 B2 6/2016 Size et al.
9,522,040 B2 12/2016 Anhoeck et al.
9,603,614 B2 3/2017 Schurr et al.
9,957,356 B2 5/2018 Zhang et al.
10,166,024 B2 1/2019 Williamson, IV
10,660,643 B2 5/2020 Kubiak et al.
11,013,518 B2 5/2021 Zhong
11,046,747 B2 6/2021 Wong et al.
11,413,050 B2 * 8/2022 Shikhman .............. A61B 17/10
2005/0165423 A1 7/2005 Gallagher et al.
2005/0216036 A1 9/2005 Nakao
2005/0234297 A1 10/2005 Devierre et al.
2006/0235457 A1 10/2006 Belson
2007/0213747 A1 9/2007 Monassevitch
2007/0219571 A1 9/2007 Balbierz
2007/0270644 A1 11/2007 Goldfarb et al.
2008/0214893 A1 9/2008 Tartaglia et al.
2010/0010511 A1 1/2010 Harris et al.
2012/0059400 A1 3/2012 Williamson
2012/0095480 A1 4/2012 Jugenheimer et al.
2012/0245693 A1 9/2012 Gorek
2015/0201947 A1 7/2015 Hill et al.
2015/0257757 A1 9/2015 Powers et al.
2016/0192996 A1 7/2016 Spivey et al.
2017/0105726 A1 4/2017 Smith et al.
2018/0008447 A1 1/2018 Jacobs et al.
2018/0036008 A1 * 2/2018 Ramsey ............... A61B 17/083
2018/0206711 A1 7/2018 Piskun
2019/0167075 A1 6/2019 Fischer et al.
2020/0315436 A1 10/2020 Pansky et al.
2020/0397445 A1 12/2020 Shikhman et al.
2022/0401107 A1 * 12/2022 Shikhman .......... A61B 17/1285
2023/0389784 A1 * 12/2023 Shikhman, et al. ......................... A61B 1/00128
2024/0090904 A1 * 3/2024 Shikhman ............ A61B 17/083
2024/0138836 A1 * 5/2024 Shikhman, et al. ......................... A61B 17/1227

FOREIGN PATENT DOCUMENTS

WO WO 2001/035832 5/2001
WO WO 2019/135958 7/2019

OTHER PUBLICATIONS

International Search Report And Written Opinion PCT/US18/67432 Dated Jun. 25, 2019.
International Search Report And Written Opinion PCT/US21/53685 Dated Feb. 23, 2022.
International Search Report And Written Opinion PCT/US22/27979 Dated Sep. 22, 2022.

* cited by examiner

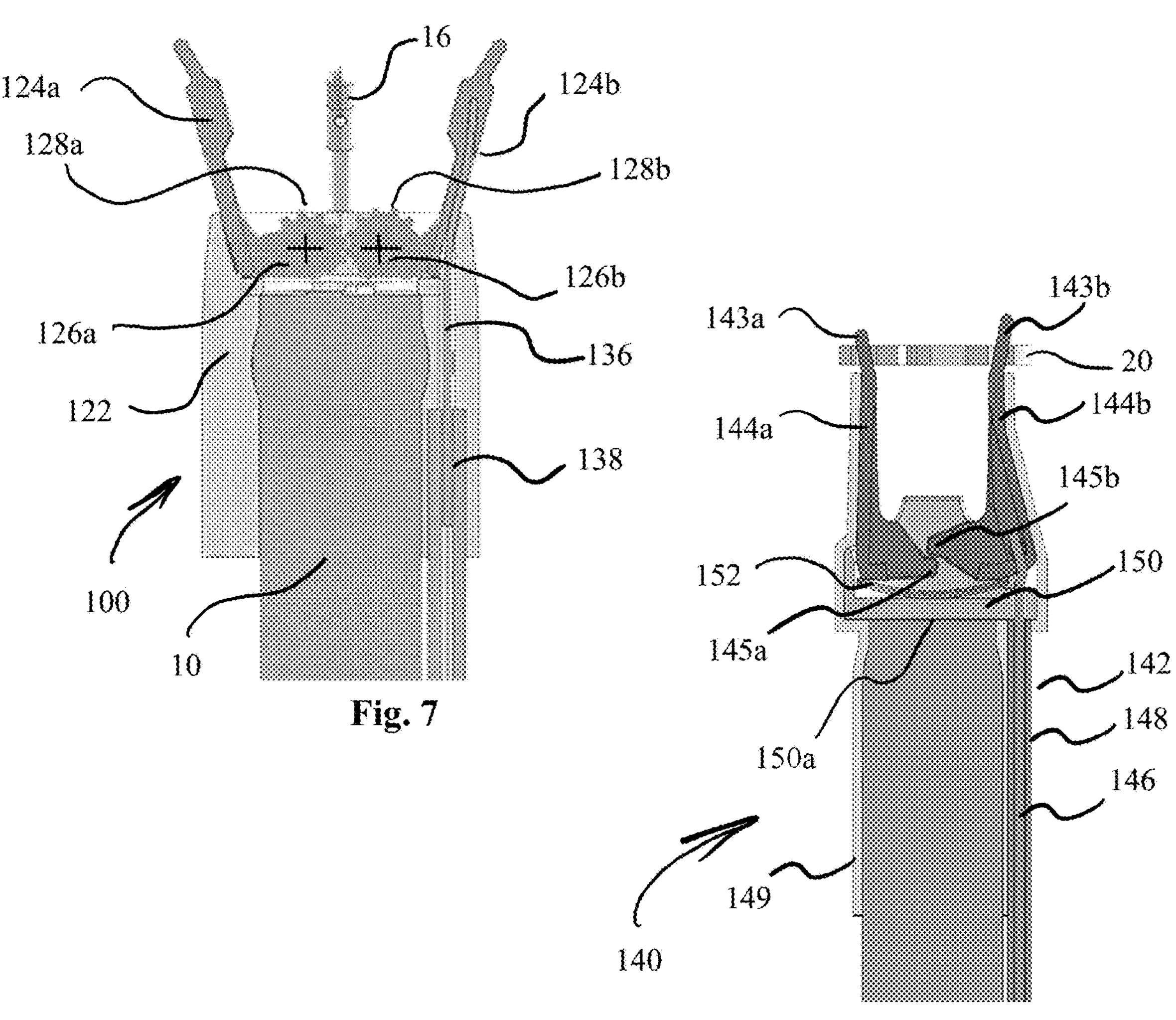
Fig. 7
Fig. 7a
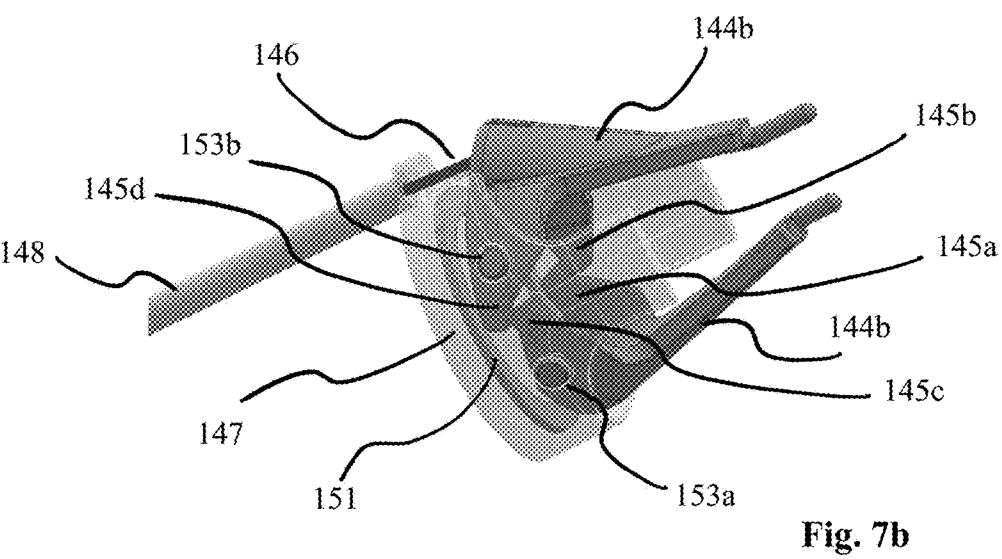
Fig. 7b

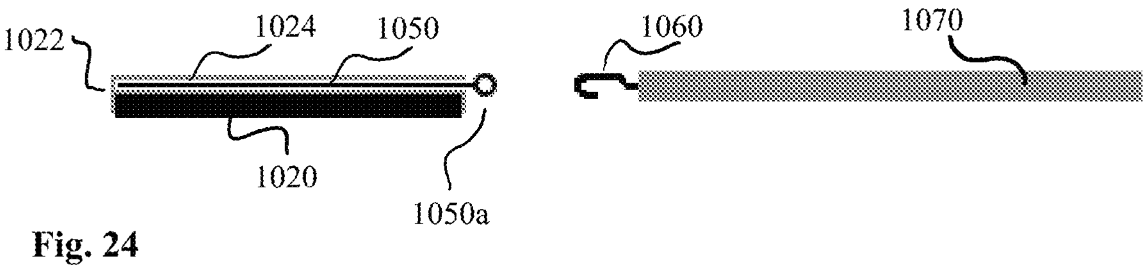
Fig. 24
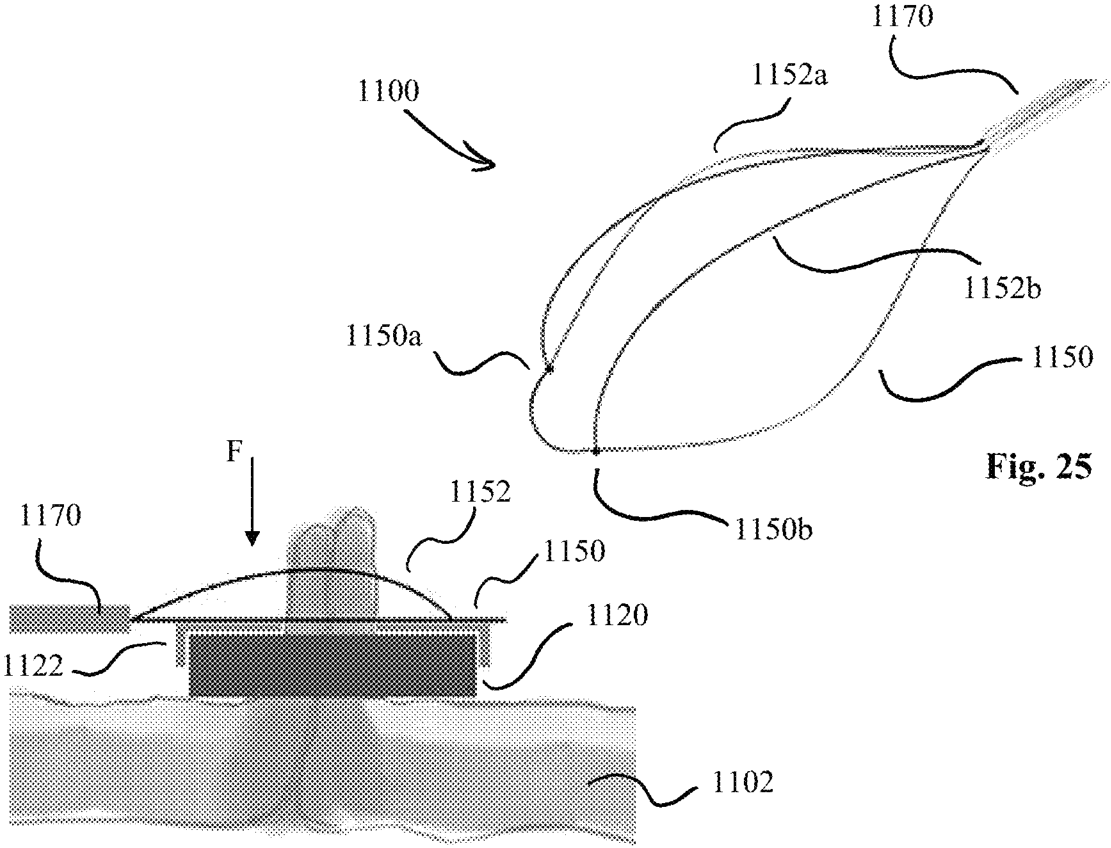
Fig. 25
Fig. 26
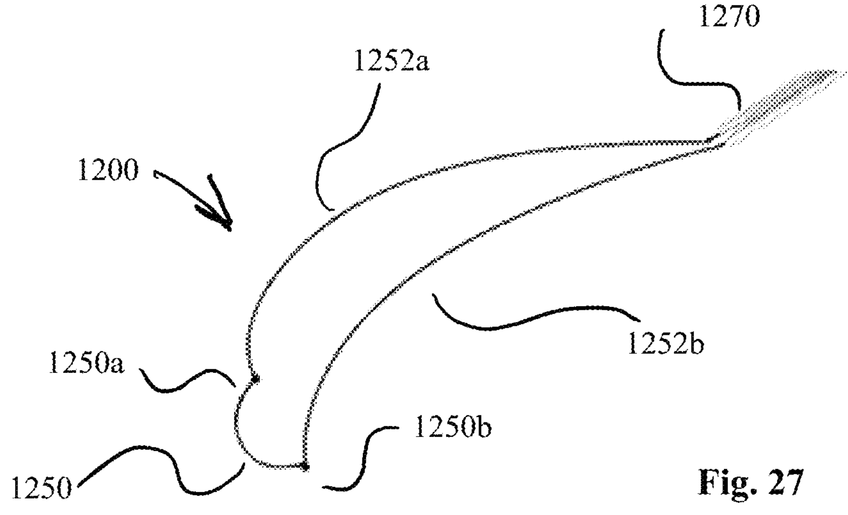
Fig. 27

1320
1322

1324
1325
1325
1320
1322
1326

1432a
1430
1432b 1400
1432a
1422a
1420
1430
1432b
1422b

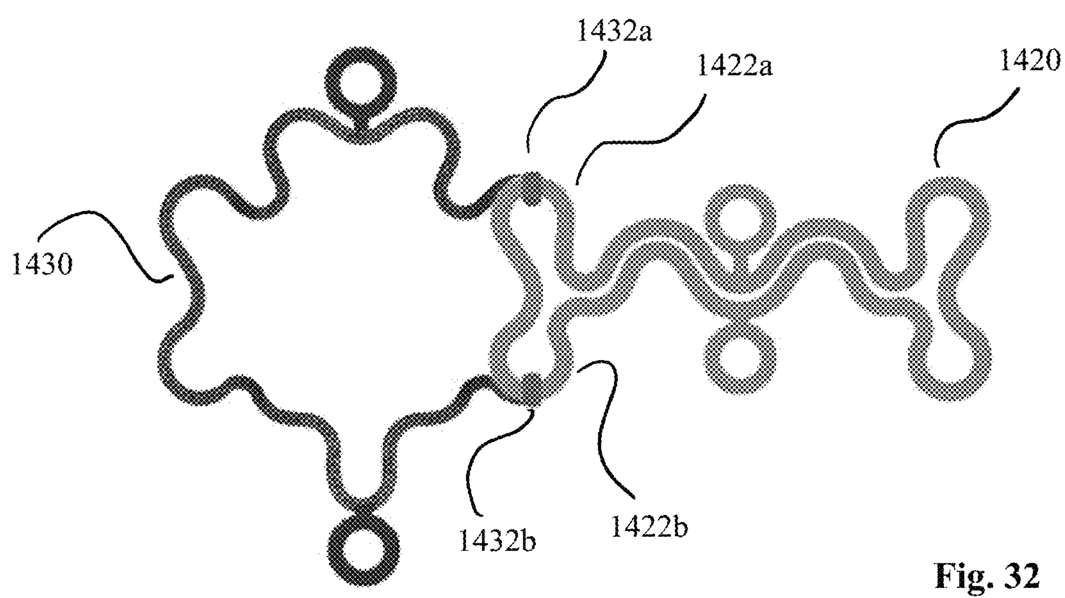
Fig. 32
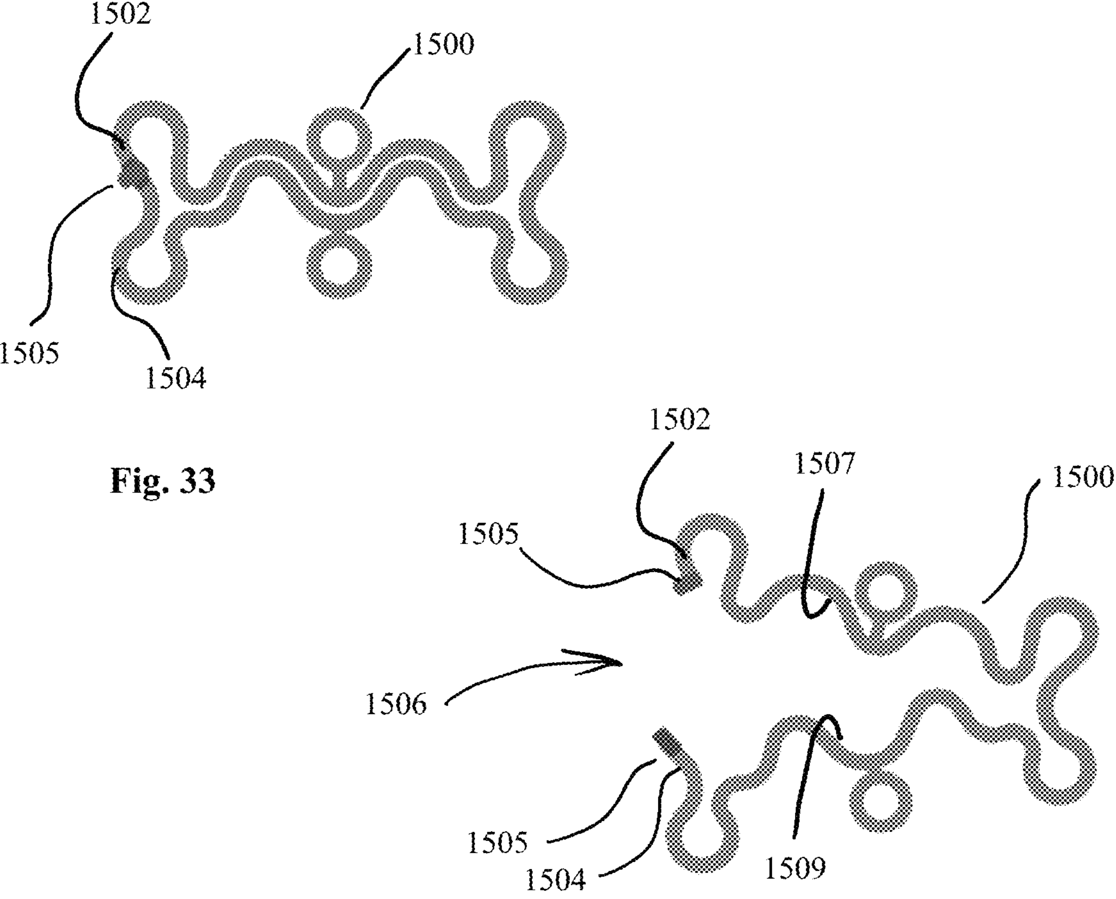
Fig. 33
Fig. 34

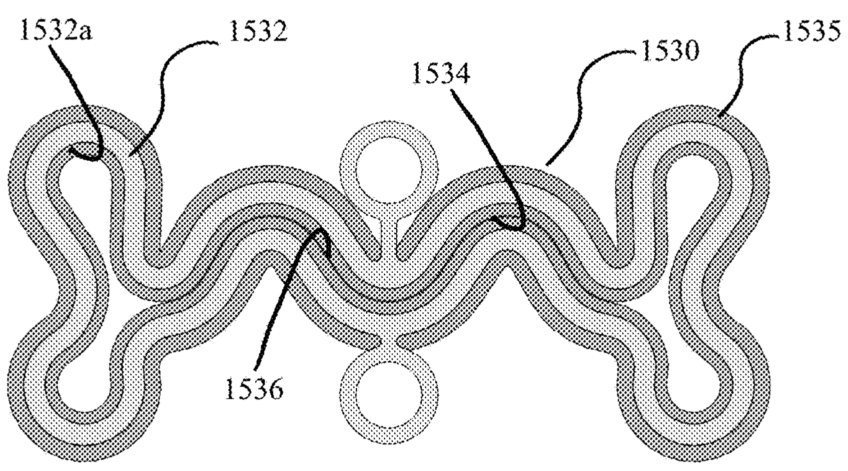
Fig. 35
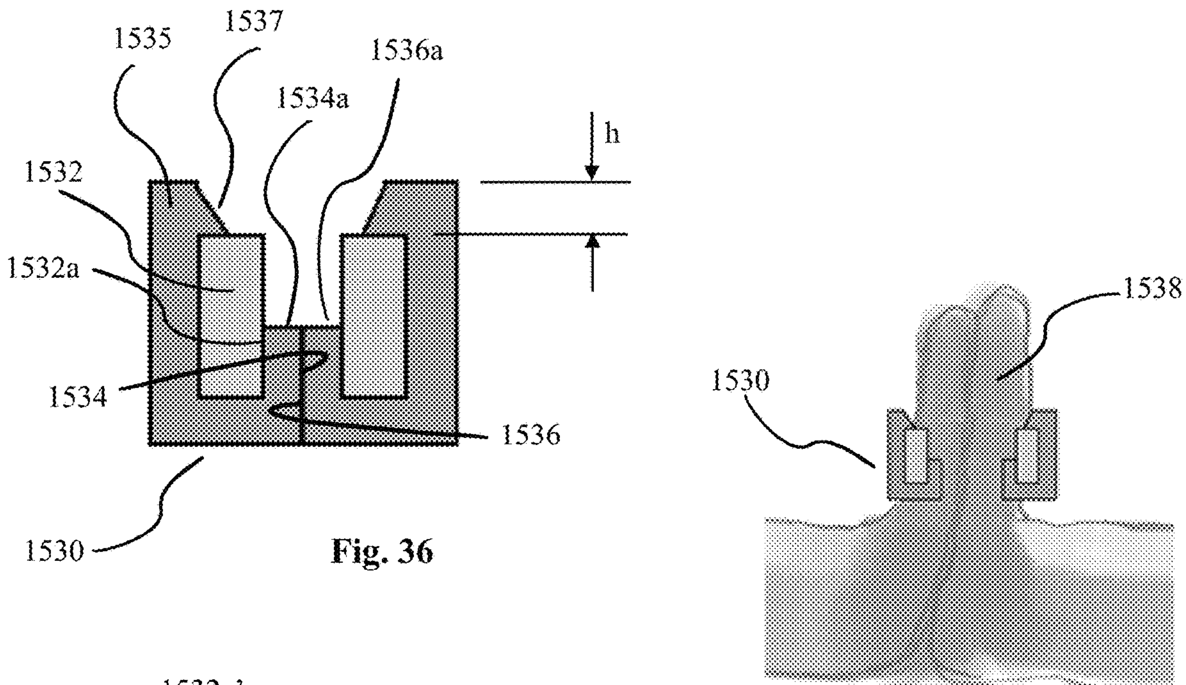
Fig. 36
Fig. 36a
1532a'
1534'
1536'
1532'
1535'
Fig. 36b

SURGICAL CLIP AND DEPLOYMENT SYSTEM

This application is a 371 of PCT application serial no. PCT/US22/27979, filed May 6, 2022, which claims priority to provisional applications 63/186,887, filed May 11, 2021, and 63/253,227, filed on Oct. 7, 2021, and this application is a continuation-in-part of application Ser. No. 16/772,454, filed Jun. 12, 2020, now U.S. Pat. No. 11,413,050, which is a 371 of PCT application serial no. PCT/US18/67432, filed Dec. 23, 2018, which claims priority to provisional applications 62/648,593, filed Mar. 27, 2018, 62/648,586, filed Mar. 27, 2018, and 62/613,902, filed Jan. 5, 2018. The entire contents of each of these applications are incorporated herein by reference.

BACKGROUND OF THE INVENTION

1. Field of the Invention

This application relates to surgical clips and endoscopic clip delivery systems mountable over endoscopes.

2. Background

Clips for closing defects in the GI tract are known. In one approach, clips are inserted through a working channel in an endoscope. However, this approach has the disadvantage of the size of the clip being limited since it must be dimensioned to fit through the small dimensioned working channel of the scope. Additionally, the instrument for delivering the clip must also be of small diameter since it also has to fit through the working channel. If the clip delivery instrument has jaws, the range of the jaws is limited due to the size limitations of the working channel. With the size restrictions, the clip in certain applications is unable to fully clamp the vessel or tissue, resulting in insufficient tissue clamping and/or requiring multiple clips to be applied which adds to the time, cost and complexity of the surgical procedure.

In another approach, disclosed in U.S. Pat. No. 6,428,548, a clip is provided with opposing grasping surfaces and joints connecting the ends of the grasping surfaces. The clip is placed on an outer surface of an endoscope cap with the cap applying a force that retains the clip in the tissue receiving (open) position. To apply the clip to tissue, the clip is deployed off of the endoscope cap so the force is no longer applied against the grasping surface so the joints due to their stored potential energy return the grasping surfaces to the grasping position to compress tissue between the grasping surfaces. This approach also has several disadvantages. First, there is no controlled opening or closure of the clip since the clip is biased open by the endoscope cap and springs back to a closed position when deployed off the cap. Second, due to the positioning of the clip over the cap, and once tissue is pulled into the cap and the opened clip, visualization is compromised. Third, once the clip is released onto tissue, it cannot be re-opened and repositioned.

The need therefore exists for a compression clip and delivery system for closing defects in the GI tract, as well as for other clinical applications, that are of sufficient size, enable controlled opening and/or closing of the clip, improve visibility so the clinician can ensure proper tissue apposition prior to release/disengagement, retraction and clip application and can be reengaged, re-opened and repositioned if the clinician determines that the initial positioning of the clip is not optimal/desirable.

For tissue compression, clips need to be designed so as to apply sufficient compression force to tissue to reduce leakage and promote healing without applying so much force that it causes unwanted tissue necrosis. The need therefore exists for a clip to strike the appropriate balance between these two competing factors. This also needs to be balanced with the clip retention force, i.e., the force that would be required to remove the clip off the tissue without opening it. The compressive force of 0.01 to 20 lbs. is contemplated.

SUMMARY

The present invention advantageously provides a surgical tissue-compression clip for compressing tissue which can be controllably moved from a closed to an open position and/or controllably moved from an open position to a closed position. In some embodiments, the clip is delivered by an endoscope. In other embodiments, the clip is delivered laparoscopically, i.e., delivered by an instrument minimally invasively. The clip can also be used in some embodiments in open surgery. The clip in preferred embodiments can further advantageously be removed and repositioned after placement on body tissue.

Commonly assigned co-pending application Ser. No. 16/772,454, filed Jun. 12, 2020 (Publication No. 2020/0397445), the entire contents of which are incorporated herein by reference, discloses clips which achieve the foregoing. The present invention provides additional inventive clip concepts which provide one or more of the following additional advantages: a) improve/optimize the compression force; b) lengthen the clip to allow for closure of larger defects; c) separate the clip; d) increase tissue retention; and/or e) enhance separation of healthy and unhealthy tissue to be resected. Note that the clips disclosed herein could have one or any number of the foregoing five features/advantages.

The present invention also provides a clip delivery system and method for delivering the endoscopic clip which is easily mountable over an endoscope and provides controlled manipulation. Commonly assigned co-pending application Ser. No. 16/772,454 discloses various clip deployment systems for effectively applying the endoscopic clip The present invention provides additional inventive clip deployment concepts which provide one or more of the following additional advantages: 1) simplify the system; 2) reduce the rigidity of the system; 3) facilitate mounting to the endoscope; 4) facilitate reorientation of the clip; and/or 5) facilitate certain surgical procedures via enhancing instrument access. Note that the clip deployment systems disclosed herein could have one or any number of the foregoing five features/advantages and can be used for applying clips having one or more of the five features/advantages enumerated above.

In accordance with one aspect of the present invention, a surgical clip for compressing body tissue is provided comprising a first tissue contacting surface and a second tissue contacting surface, the clip having a closed position (preferably normally closed position) wherein the first and second tissue contacting surfaces are in contact with each so there is no gap between the first and second contacting surfaces. The clip is movable to a radially expanded open position wherein the first and second tissue contacting surfaces are spread away from each other, wherein, in preferred embodiments, in the closed position the clip has a preload, i.e., a compressive force between the first and second tissue contacting surfaces.

In accordance with another aspect of the present invention, a surgical clip for compressing body tissue is provided comprising a first tissue contacting surface and a second tissue contacting surface, the clip having a closed position (preferably normally closed position) wherein the first and second tissue contacting surfaces are spaced a distance apart, but the gap is less than the thickness of the tissue on which the clip is applied. The clip is movable to a radially expanded open position wherein the first and second tissue contacting surfaces are spread away from each other, wherein in the closed position the clip is configured to apply a compressive force to tissue. Thus, compression force is present between the first and second tissue contacting surfaces even when there is a gap between them due to tissue thickness. In other words, in the embodiment with a gap, there is no preload and no compression/compressive force between the first and second tissue contacting surfaces unless the thickness of tissue is greater than the gap between the tissue contacting surfaces. (In the preferred embodiments with no gap, there is a preload/compression force between the tissue contacting surfaces).

In accordance with another aspect of the present invention, a system for compressing body tissue is provided comprising a surgical clip and a clip deployment device or system. The surgical clip has a first tissue contacting surface and a second tissue contacting surface, the clip movable from a closed position to an open position, and in the open position the clip receives tissue between the first and second tissue contacting surfaces and in the closed position the clip compresses tissue between the first and second tissue contacting surfaces. In endoscopic embodiments, the clip deployment device has an endoscope engaging member and a first clip engagement member and a second clip engagement member engageable with the clip, the endoscope engaging member engaging a distal portion of the endoscope. At least one of the clip engagement members is movable, and in preferred embodiments pivotable, with respect to the endoscope engaging member and movable between first and second positions to controllably move the clip from the closed position to the open position and/or controllably move the clip from the open position to the closed position. The clip both opens and deforms so a geometry of the tissue contacting surfaces changes when moving from the closed to the open position. In laparoscopic and open surgery embodiments, such clip would not be mounted to an endoscope but delivered and controlled by an instrument having at least one movable, preferably pivotable, clip engagement member.

In accordance with another aspect of the present invention, a system for compressing body tissue is provided comprising a surgical clip and a clip deployment device or system. The surgical clip has a first tissue contacting surface and a second tissue contacting surface, the clip movable from a closed position to an open position. In the open position, the clip receives tissue between the first and second tissue contacting surfaces and in the closed position the clip compresses tissue between the first and second tissue contacting surfaces. In endoscopic embodiments, the clip deployment device has an endoscope engaging member and a first actuator for a first clip engagement member. In some embodiments, it also has a second actuator for a second clip engagement member, the clip engagement members engageable with the clip. The actuators in some embodiments can extend through a respective channel in the endoscope engagement member. The endoscope engaging member engages at least a portion of the endoscope. The engagement can be at a distalmost end, a distal portion, e.g., spaced one or a few inches from the distalmost end, or at other portions of the endoscope. The first and second clip engagement members controllably move the clip from the closed position to the open position and/or controllably move the clip from the open position to the closed position, the clip deforming so a geometry of the tissue contacting surfaces changes when moving from the closed to the open position. Movement of the clip to the open position spreads the clip to create a gap, or increase an already existing gap, between the first and second tissue contacting surfaces and the open clip receives a first and second endoscopic instrument therethrough to pull tissue into the gap.

In accordance with another aspect of the present invention, a method of placing a surgical clip on tissue and applying a compressive force to tissue, is provided comprising:

a) mounting a clip deployment device or system over an endoscope;
b) inserting the endoscope and clip deployment device with a clip mounted onto it to target tissue;
c) moving, and preferably pivoting, at least one of a first clip engagement member and a second clip engagement of the clip deployment device to apply a force to first and second sides of the clip to move the clip from a closed position to an open position to spread opposing tissue contacting surfaces of the clip;
d) inserting at least one tissue grasping (tissue acquisition) device through a space in the open clip;
e) grasping/acquiring tissue and pulling/placing it through a space in the open clip: and
f) moving the first and second clip engagement members to controllably move the clip to the closed position.

In some embodiments, the tissue grasping device is inserted through a channel in the clip deployment device; in other embodiments, the tissue grasping device is inserted through a channel of the endoscope; and in other embodiments one tissue grasping device is inserted through a channel in the clip deployment device and another tissue grasping device is inserted through a channel of the endoscope. The channel in the clip deployment device can be angled inwardly so the instrument angles toward the space in the open clip.

In some embodiments, the clip deployment device includes a conduit/channel attached to the side of the endoscope and a clip opening device, such as a grasper that can open the clip, introduced into/through the conduit when the scope is already inserted.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 7 is a cross-sectional view of an alternate embodiment of the delivery system of the present invention for deployment of an endoscopic clip;

FIG. 7*a* is a cross-sectional view of an alternate embodiment of the delivery system of the present invention for deployment of an endoscopic clip with an elastomeric shield over the delivery system;

FIG. 7*b* is a perspective view of the system of FIG. 7*a*, the elastomeric shield removed for clarity;

FIGS. 15-18 are side views illustrating clip-guided resection procedures using various clip configurations wherein:

FIG. 24 shows an alternative embodiment of a clip with an integrated tissue cutting/resection device;

FIG. 25 is a perspective view of an alternate embodiment of a snare for dissection of tissue;

FIG. 26 is a side view showing the snare of FIG. 25 inserted over the spacer of FIG. 16*a;*

FIG. 27 is a perspective view of an alternate embodiment of a snare for dissection of tissue;

FIG. 32 is a view similar to FIG. 31 showing the clip extension in the open position and the clip in the closed position;

FIG. 33 is a top view of an alternate embodiment of a clip having a disengagement mechanism to separate the clip;

FIG. 34 is a view similar to FIG. 33 showing the clip disengagement mechanism open to separate the clip;

FIG. 35 is a top view of an alternate embodiment of the clip of the present invention having a cover to aid in application of a compressive force;

FIG. 36 is a cross sectional view of the clip of FIG. 35;

FIG. 36*a* is a side view of the clip of FIG. 36 placed over tissue;

FIG. 36*b* is a cross sectional view of an alternative embodiment of the clip of FIG. 35;

DETAILED DESCRIPTION OF PREFERRED EMBODIMENTS

Figures 1, 2, 3:
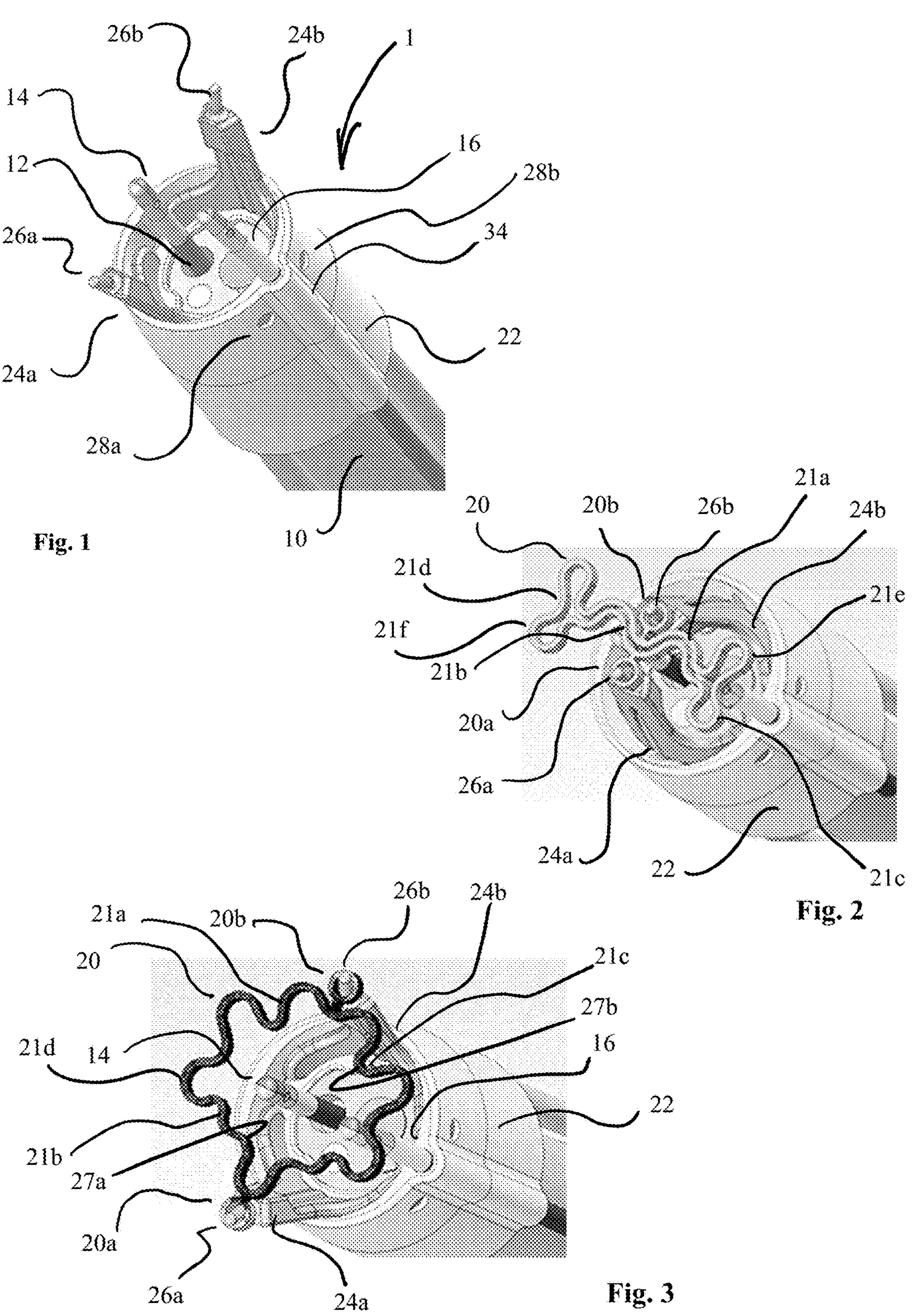
FIG. 1 is a perspective view of an embodiment of a delivery system of the present invention for deployment of an endoscopic clip.
FIG. 2 is a view similar to FIG. 1 showing one embodiment of a clip held in the jaws of the delivery system of FIG. 1.
FIG. 3 is a view similar to FIG. 2 illustrating opening of the clip by pivoting of the jaws outwardly.

The present invention provides a system and method for closure of wall defects in hollow organs, such as a colon, esophagus, stomach etc. The system includes a surgical clip and a deployment device for delivering the surgical clip to tissue and manipulating the clip between closed and open positions by applying a force to opposing sides of the clip. In one approach/aspect, the clips of the present invention are radially expandable from a closed position to an open position to enable tissue to be positioned within an opening in the clip, and then returnable to the closed position to compress tissue between opposing compression surfaces or points of the clip. Various embodiments of the radially expandable clips are discussed in detail below. Such radial expansion deforms/changes the geometry of the tissue contacting/engaging surfaces and/or the side surfaces of the clip as it moves to the open position.

The opening of the clip is controlled by a clip deployment device (also referred to herein as a clip deployment system) which is preferably mountable over an endoscope and has clip engagement members, e.g., jaws, actuable by the clinician outside the patient, such actuation applying a force to opposing sides of the clip to spread the tissue contacting surfaces of the clip apart. The control of the clip enables the clip to be reengaged/reconnected, reopened and repositioned if necessary during the surgical procedure. The clip engagement members additionally allow for controlled closure of the clip if desired. The controlled movement can be continuous through the opening and closing. Alternatively, it can be controlled in discrete increments between the open and closed positions. Various embodiments of the clip deployment device are discussed in detail below in conjunction with the method of use.

The clips of the present invention can be delivered by an endoscope as the clip deployment device is in the form of a sheath, cap or support placed over or in abutment with an endoscope. In this manner, the clips of the present invention can be delivered by a conventional endoscope. The sheath, cap or support includes and/or supports the clip engagement members for clip manipulation as described below.

In alternate embodiments, the clips of the present invention are delivered laparoscopically by a clip supporting and delivery instrument without mounting to an endoscope. In still other embodiments, the clips are delivered by a clip supporting and delivery instrument in open surgical procedures.

The delivery device of the present invention is able to open or close the clip on demand allowing the user to control its deployment. The clip could be closed over the target tissue slowly and gently to minimize unnecessary tissue damage due to impact of instant/fast "snap" closure, over compression or excessive spring closing force on tissue. The clip can be deformable or normally in a closed position. The user can visually confirm that the clip captures tissue appropriately and circumferentially before the delivery device is disengaged/disconnected leaving the clip in place. If necessary, the user can re-open and reposition the clip if its location is not satisfactory. The clip is configured to allow an engagement/reengagement with the clip actuating members e.g., jaws, of the delivery system even after the clip is deployed and the delivery system separated from the clip. The actuating members can in some embodiments be operated independently, i.e., actuated separately, such that the actuating member applies an opening force to a side of the clip that it is connected to. In other embodiments, the actuating members are actuated together to apply the opening force to both sides of the clip simultaneously or substantially simultaneous. After the clip is delivered and its proper placement is confirmed, the actuating members are disengaged from the clip. In other words, in some embodiments, the force to open the clip could be applied to just one side of the clip, while the other side is held stationary or substantially stationary (minimal movement) to apply a holding force and in other embodiments the force could be applied to both sides of the clip either simultaneously or one side at a time.

An alternative embodiment of a delivery device that only has one clip actuating member engaged with a first clip engagement member, while the other side is held stationary or substantially stationary by an external/separate/independent device/member/support, for example an endoscopic instrument that is introduced via a working channel of the endoscope, is also contemplated. In such embodiment, the external member can be considered a second clip engagement member.

In some embodiments, the clip is designed with increased compressive force so that the tissue contacting surfaces of the clip form tissue compressing surfaces to apply a sufficient compressive force on tissue to avoid leakage and promote healing without causing unwanted tissue necrosis. This increased compressive force can be achieved through clip geometry, clip manufacture, e.g., heat treating and/or supplemental components/features, each described in detail below. In other embodiments, the compressive force on tissue is intentionally excessive to promote necrosis and tissue sloughing off.

Clip-guided resection (sometimes referred to as "Clip-assisted EFTR (endoscopic full-thickness resection)") is emerging as a new, easier, and potentially safer alternative to EMR (endoscopic mucosal resection) and ESD (endoscopic submucosal dissection) that involves securing the defect before providing full-thickness resection of lesions ("close then cut"). The clips and systems of the present invention can be utilized in such procedures, as in well as in other procedures. The systems and clips of the present invention can be inserted through the esophagus or colon, as well as through other body cavities.

The systems of the present invention can be retrofitted to a conventional endoscope if desired.

The systems of the present invention can also be retrofitted to a robot, e.g., a robotic arm, similar to that currently being utilized for endoluminal surgery. In this manner, one or more of the actuators for moving the clip engagement members could be remotely robotically controlled.

It should be understood that features described for one of the embodiments could also be beneficial and utilized for other embodiments.

As used herein, the term "proximal" refers to the portion, region or component closer to the user and the term "distal" refers to the portion, region or component further from the user.

As noted above, the clips of the present invention provide one or more of the following advantages: a) improve the compression force; b) lengthen the clip; c) separate the clip; d) increase tissue retention; and/or e) enhance separation of healthy and unhealthy tissue to be resected. As noted above, the clip delivery systems and methods of the present invention for delivering the endoscopic clip provide one or more of the following advantages: 1) simplify the system; 2) reduce the rigidity of the system; 3) facilitate mounting to the endoscope; 4) facilitate reorientation of the clip; and/or 5) facilitate certain surgical procedures via enhancing instrument access. Such advantages will become apparent from the detailed description below. Note that through the various disclosed embodiments, some embodiments may have any number of these features, e.g., only one, only two, etc.

Turning now to the drawings wherein like reference numerals identify similar structural features of the clips, several embodiments of the clip and clip deployment systems will be described. Note clip delivery "system" and clip delivery "device" are used interchangeably herein. The clip delivery system is also referred to herein as the clip deployment system or device. Note "endoscope engagement member" includes a sheath, cap platform or support (or strap, tape, etc.) which either secures the delivery system to the endoscope or is in abutment or in contact with the endoscope without such securement.

In some embodiments, the delivery system is placed right in front of and/or coaxially to the endoscope. However, other positions of the delivery system relative to the scope, for example eccentric/partially off-center of the scope or partially or completely outside/radially displaced relative to the scope body, are also contemplated.

Turning initially to FIGS. 1-5, a delivery system for deployment of an endoscopic clip in accordance with one embodiment of the present invention is illustrated. Clip delivery system (device) 1 includes an endoscope engagement member in the form of a distal cap 22 that is placed over the distal end of an endoscope 10. Cap 22, as well as the other embodiments of the caps disclosed herein, can be of various lengths to cover various lengths of the endoscope and can be frictionally fit over the endoscope 10 for securement thereto. In the illustrated embodiment, the cap 22 covers a distal portion of the endoscope 10 but could alternatively cover a greater length of the endoscope than shown. Cap 22 has a flange or rim 22*a* extending inwardly (FIG. 4) which provides a distal stop for the endoscope 10 as it abuts the proximal surface of rim 22*a*.

Figures 4, 5, 5A, 6:
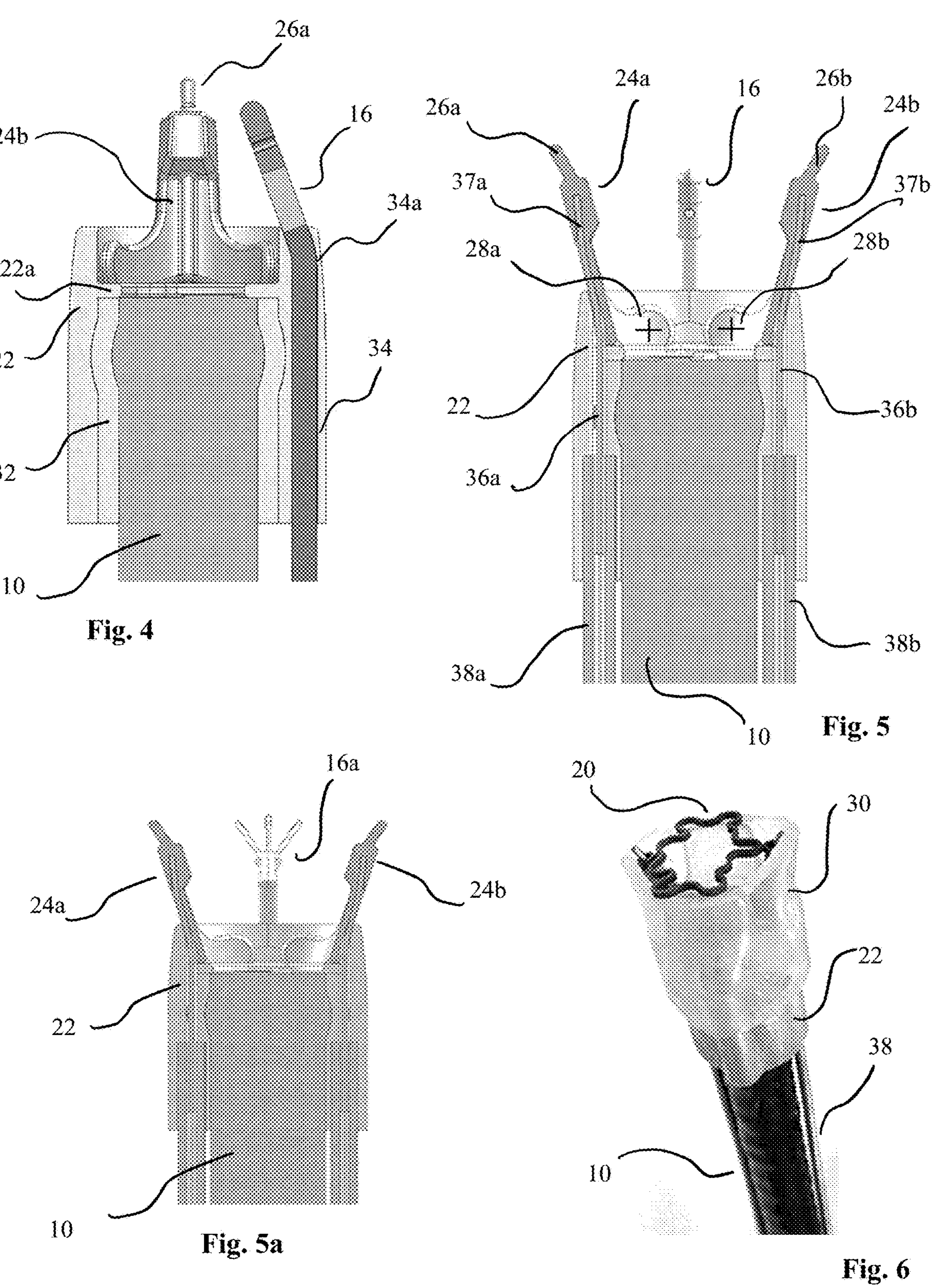
FIG. 4 is a cross-sectional view of the distal portion of the delivery system of FIG. 1.
FIG. 5 is another cross-sectional view of the distal portion of the delivery system of FIG. 1.
FIG. 5*a* is a view similar to FIG. 5 illustrating a double-action grasper inserted through the working channel of the endoscope.
FIG. 6 is a perspective view of an alternate embodiment of the delivery system of the present invention having an elastomeric shield over a cap of the delivery system.

The clip delivery system 1 includes two clip engagement members to engage the clip in the form of two jaws 24*a* and 24*b* that are movable, preferable pivotable, within the cap 22. The jaws 24*a*, 24*b* are on the distal surface of rim 22*a* of cap 22 and are pivoting relative to the pivot pins 28*a* and 28*b*. At the distal end of the jaws 24*a* and 24*b* are pins 26*a* and 26*b* (or other elongated structure) configured and dimensioned for engagement with an endoscopic clip. As shown in FIG. 5, the pins 26*a*, 26*b* preferably angle slightly outwardly from the longitudinal axis of the cap 22 and a longitudinal axis of the jaw from which they extend. This increases the retention force on the clip when it is held on the pins 26*a*, 26*b* during delivery/insertion. The pins 26*a*, 26*b* are in alignment with their respective jaw 24*a*, 24*b* as shown in the cross-sectional orientation of FIG. 4.

The cap 22 can have an external channel 34 for receipt of an endoscopic instrument. The channel 34 can be angled at a distal end as shown so the instrument as it exits from the channel 34*a* angles, i.e., angles relative to the longitudinal axis of the cap 22 (e.g., angles inwardly toward the axis), into the space in the open clip. More than one external channel can be provided to receive additional endoscopic instruments. In FIG. 1, the clip delivery system 1 has one external channel 34 while another instrument can be inserted through a working channel of the endoscope. For example, an endoscopic tissue grasping (tissue acquisition) device such as a tissue grasper 14 with two jaws is shown introduced/inserted through an instrument channel of the endoscope 10 while an endoscopic tissue grasping (tissue acquisition) device such as a tissue grasper 16 with two jaws is shown inserted through the external channel 34. The graspers 14, 16 are used for tissue acquisition. By using the scope channel for introduction of one of the graspers, the overall transverse dimension of the cap can be reduced. The channel can have a bend 34*a* to enable the instrument to go toward/through the open clip. The instrument exiting the channel can be outside the closed clip and when the clip is open and directed inside the clip for passage of the instrument through the open clip.

In an alternate embodiment shown in FIG. 5*a*, a double-action grasper 16*a* can be inserted through the endoscopic channel. Such grasper can have three jaws, with the middle jaw fixed and the two outer jaws controlled independently. In use, the endoscope would be directed to one edge and the grasper would grip the edge between a first outer jaw and the middle jaw. The scope would then be directed to the other edge and the second outer jaw would grip the tissue between it and the middle jaw, thus approximating the tissue and pulling it into the space in the open clip.

FIG. 2 illustrates the delivery system 1 with a clip 20 connected to (supported by) the jaws 24*a* and 24*b* by insertion of the pins 26*a* and 26*b* into the clip receiving portions of the clip 20 which in the FIG. 2 embodiment are in the form of eyelets 20*a* and 20*b*. Eyelets 20*a*, 20*b* are on opposing sides of the clip 20. Clip 20 is in the normally closed position (FIG. 2) and is moved by the jaws 24*a* and 24*b* to an open position against the bias of the clip 20 as shown in FIG. 3. Clip 20 is moved to the open position by pivoting the jaws 24*a* and 24*b* outwardly (away from the longitudinal axis of the cap 24 and endoscope 10). As the clip 20 is opened by this pivoting movement, this pivoting movement not only spreads the clip in multiple directions but also deforms the clip in multiple directions so that its geometry changes. More specifically, the opposing tissue engaging/contacting/compressing surfaces 21*a*, 21*b* are in a first wavy/non-linear (uneven/irregular) geometry/configuration in the closed position of the clip 20 and assume a different wavy/non-linear (uneven/irregular) geometry/configuration in the open position. Further, the side surfaces (edges) 21*c*, 21*d* of clip 20 also change configuration/geometry as the clip 20 is opened as can be appreciated by comparing FIGS. 2 and 3. Loops at the side edges of the clip, e.g., loops 21*e* and 21*f*, also change in radius and size. Thus, multiple points of the clip are spread/stretch in multiple radial directions away from the center point of the clip and thus distances from the center point not just of the tissue compression surfaces but the side surfaces change in relation to the center point. As can be appreciated by comparing FIGS. 2 and 3, the tissue compression surfaces of the clip have multiple curved surfaces in the open and closed position, and these curved surfaces change in geometry/radius as the clip opens. Also, by comparing these Figures, it can be appreciated that as the clip spreads to an open position, the curved surfaces, the "loops" and "waves" of the sides "open up"/deform/increase in radii as the peaks and valleys of the tissue compressing surfaces alter. The compression force on tissue of the tissue engaging surfaces is discussed in more detail below.

As shown, the clip is held distal or mostly distal of the endoscope engaging member so it is distal of the distal end of the endoscope. Other clip locations relative to the endoscope engaging members, including lateral and proximal are also contemplated.

The jaws 24*a* and 24*b* pivot relative to pivot points 28*a* and 28*b*, respectively (FIGS. 1 and 5). The jaws 24*a* and 24*b* are operated from the proximal end of the system by actuators (actuating members) in the form of control cables, for example, push-pull cables, 36*a*, 36*b*, respectively, that are positioned within the conduits (channels) 38*a* and 38*b* of cap 22. The control cables 36*a*, 36*b* as shown extend through and distally of the conduits 38*a*, 38*b* of cap 22, and attach to the jaws 24*a*, 24*b* by crimping, welding, or other means of attachment preferably at distal regions 37*a*, 37*b*, respectively. Pulling of the cables 36*a*, 36*b* proximally pivots the jaws outwardly to open clip 20; pushing the cables 36*a*, 36*b* distally pivots the jaws inwardly to close the clip 20. In alternate embodiments, pulling of the cables 36*a*, 36*b* proximally pivots the jaws inwardly to close clip 20; pushing the cables 36*a*, 36*b* distally pivots the jaws outwardly to open the clip 20. Alternatively, the cables 36*a* and 36*b* could work to pull the jaws 24*a* and 24*b* outwardly, while springs (not shown) could push (bias) the jaws 24*a*, 24*b* inwardly. Alternatively, pull cables could be used for opening the jaws, while spring members, for example compression springs (not shown), could be used for closing the jaws.

When the clip 20 is radially expanded, the tissue grasping (tissue acquisition) devices 14 and 16 are pointed within the body of the open clip (FIG. 3). That is, they extend within the space created within the open clip, and can extend distally past the open clip 20 if desired. (The clip in the illustrated embodiment forms a closed loop). When the tissue graspers 14 and 16 acquire/grasp tissue, they can pull the tissue into the gap/space within the body of the open clip 20. As discussed above, the clip 20 is radially expandable by jaws 24*a*, 24*b* as the opposing tissue engaging surfaces 27*a*, 27*b* are moved away from each other. It should be appreciated that FIGS. 2 and 3 show one example of a clip that can be utilized; it should be appreciated that other clips such as such as those disclosed in commonly owned co-pending application Ser. No. 16/772,454, filed Jun. 12, 2020, the entire contents of which as noted above are incorporated herein by reference, can be utilized with the clip delivery system 1 as well as with the other various clip delivery (deployment) systems disclosed herein.

The first and second clip engagement members controllably move the clip a) from the closed position to the open position and/or b) from the open position to the closed position, the clip deforming so a geometry of the tissue contacting surfaces changes when moving from the closed to the open position. Movement of the clip to the open position spreads the clip to create a gap, or increase an already existing gap, between the first and second tissue contacting surfaces to receive a first and second endoscopic instrument therethrough to pull tissue into the gap.

It is contemplated that one or two or more than two clip engagement members can be provided.

In an alternate embodiment, one device could have an open clip preloaded/mounted on it so it doesn't need to first open the clip and then controllably close it. Thus, in these embodiments, the clip engaging members only control closure of the clip. A separate device would then need to be inserted if necessary to open the clip for removal.

The cap 22 in some embodiments can be placed over the endoscope 10 with a spacer 32 that could be made from an elastomeric material which is placed between the cap 22 and the scope 10 to create a frictional fit. The spacer 32 is preferably connected/attached to the cap 22. The endoscopic tissue grasper 16 is inserted via the channel 34 located within the wall of the cap 22.

In some embodiments, a shield is placed over the cap to cover over the edges of the clip 20 (and jaws 24*a*, 24*b*) to protect the anatomical structures, such as the colon, from accidental damage during the system insertion and operation. An example of such shield is illustrated in FIG. 6. Shield 30 is preferably made of an elastomeric material and extends over the entire cap 24, or alternatively, over a portion thereof, and extends over a portion of the endoscope 20, or in alternate embodiments over an entire length of the endoscope. The shield 30 terminates flush with the mounted clip 20 or alternatively can terminate slightly proximally of the distal surface of the mounted clip 20. The shield 30 can itself be the endoscope engagement member to provide the connection of the cap 22 to the scope 10 by its frictional fit due to its elasticity (see e.g., FIG. 7*a*) or alternatively the cap 22 can frictionally engage the scope 10 and the shield 30 supplements the cap attachment. In alternate embodiments, the cap connects to the endoscope and the shield only provides a cover without any endoscope connection function. The shield 30 provides a more flexible component compared to the more rigid cap 22 which thereby aids insertion. Note the shield can stretch as the clip is opened or alternatively the shield can be pulled proximally/retracted from a proximal end of the delivery system to expose the clip. The shield can be pulled by a control cable or other member for retraction or if the shield is of sufficient length to extend to outside the body, can be pulled by a clinician. Note the shield for the jaws and/or clip can be used in any of the embodiments disclosed herein.

FIG. 7 shows an alternative clip delivery system (device) designated generally by reference numeral 100. The system 100 has a cap 122 that is placed over the scope 10. Two jaws 124*a* and 124*b* are attached to and pivot within the cap 122 about the pivot points 126*a* and 126*b*. The jaw 124*a* has a gear 128*a*, and jaw 124*b* has a gear 128*b*. The gears 128*a*, 128*b* are engaged, such that when the jaw 124*b* is pivoted by pulling the cable 136 which extends within a channel in the jaw 124*b*, the jaw 124*a* also pivots due to the intermeshing of the teeth of gear 128*a* with the teeth of gear 128*b*. Therefore, in this manner, both jaws 124*a*, 124*b* of the system 100 are controlled by a single cable. Thus, jaw 124*b* can be considered the driving component and jaw 124*a* as the passive component which is driven (actuated) by movement of jaw 124*b* via actuation of a push-pull control cable 136 which is attached to a distal portion of the jaw 124*b* distal of the pivot point 126*b*. Cable 136 extends through conduit 138 in cap 122 which is placed over endoscope 10 and secured, for example by a friction fit. Pulling of the cable 136 can open the jaws 124*a*, 124*b*, alternatively, pushing of the cable 136 can close the jaws 124*a*, 124*b*. Jaws 124*a*, 124*b* have clip engaging pins like pins 26*a*, 26*b* of FIG. 5 to engage/connect a clip. Alternatively, a pull cable could be used for opening the jaw 124*b*, while spring member(s), for example compression spring (not shown), could be used for closing the jaws.

In an alternate delivery system 140, instead of gears to actuate the passive jaw, interaction of camming surfaces actuates the passive jaw. More specifically, as shown in FIGS. 7*a*-7*b*, camming surfaces 145*b* and 145*d* of jaw 144*b* engages camming surfaces 145*a* and 145*c* of jaw 144*a* such that when jaw 144*b* is pivoted about pin 153*a* by a control cable 146 attached to jaw 144*b* and extending within conduit 148 of support 142, it pivots jaw 144*b* about pivot pin 153*b*. Pulling of the cable 146 can open the jaws 144*a*, 144*b*, alternatively, pushing of the cable 146 can close the jaws 144*a*, 144*b*. An optional curved washer spring 152 pushes the jaws inwardly toward each other so they act simultaneously as the cam surfaces are constantly interacting with each other. As shown, cam surface 145*b* pushes down on surface 145*a* and cam surface 145*d* pushes up on surface 145*c*. Jaws 144*a*, 144*b* have clip engaging pins like pins 143*a*, 143*b* to engage/connect to the clip 20.

The system 140 of FIGS. 7*a*-7*b* also differs from the embodiment of FIG. 7 in that one of the jaw pins (or alternatively one of the jaws) is slightly longer than the other jaw pin. In the illustrated embodiment, pin 143*b* of active jaw 144*b* is longer than pin 143*a* of passive jaw 144*a*; in alternate embodiments, passive jaw pin 143*a* is longer than active jaw pin 143*b*. This differing length enables the jaws to engage eyelets of the clip one at a time—if the pin/jaws are the same height, the clinician could lose the connection to the one eyelet while trying to engage the other eyelet with the other jaw pin. Note this feature of different length jaws or pins can be utilized in any of the delivery systems disclosed herein.

The system 140 of FIGS. 7*a*-7*b* also differs from the embodiment of FIG. 7 in that it minimizes the amount of rigid material attached to the scope and utilizes an elastomeric sleeve to mount to the scope. More specifically, scope engagement member 142 of system 140 has a platform or support 150 onto which the jaws 144*a*, 144*b* are attached and a channel or conduit 148 to receive actuation cable 146. The platform 150 is placed over the scope 10 such that the tip of the scope 10 abuts the lower surface 150*a* of platform 150. Thus, the endoscope engaging member is in the form of a platform 150 that is not connected to the endoscope but is in abutment. The plastic sleeve 149 preferably made out of an elastomer is placed over the jaws 144*a*, 144*b*, platform 150 and channel 148 (if an external channel is provided) and over at least a distal end portion of the endoscope to frictionally engage the scope and thereby connect the platform 150 and jaws 144*a*, 144*b* to the endoscope. The sleeve 149 can also provide a protective shield in the same manner as shield 30 of FIG. 6. In addition, to minimize the rigid portion, in some embodiments, the sleeve 149, due to its elastomeric stretchable properties, enables the sleeve to be mounted to different sized and models of scopes. Thus, in these embodiments, the clip deployment device is kept separately from the mounting sleeve as the platform abuts the scope, and then the sleeve secures the platform to the desired diameter scope. Note although the sleeve and cap (or platform) are described as separate components in alternative embodiments, they can be the same part.

In alternate embodiments, one clip engagement member is movable while the other clip engagement member is stationary/fixed/attached to the connecting member/delivery device.

Note the cap (or platform) and jaws are configured to have the jaws as close to the scope as possible to minimize the added length to/in front of the scope. Thus, the delivery systems need to provide the balance of being sufficiently long so a sufficient amount of tissue can be grasped for clip application (if too short, not enough tissue will be grasped) but sufficiently short so as not to hinder the navigability of the scope and delivery system during insertion through the colon or other tortuous body structure (if too long, it can make navigation/insertion more difficult). The cap (or platform) and jaws also need to keep the diameter of the delivery system to a minimum i.e., to minimize any increase in diameter of the scope.

Figures 8, 9, 10, 11:
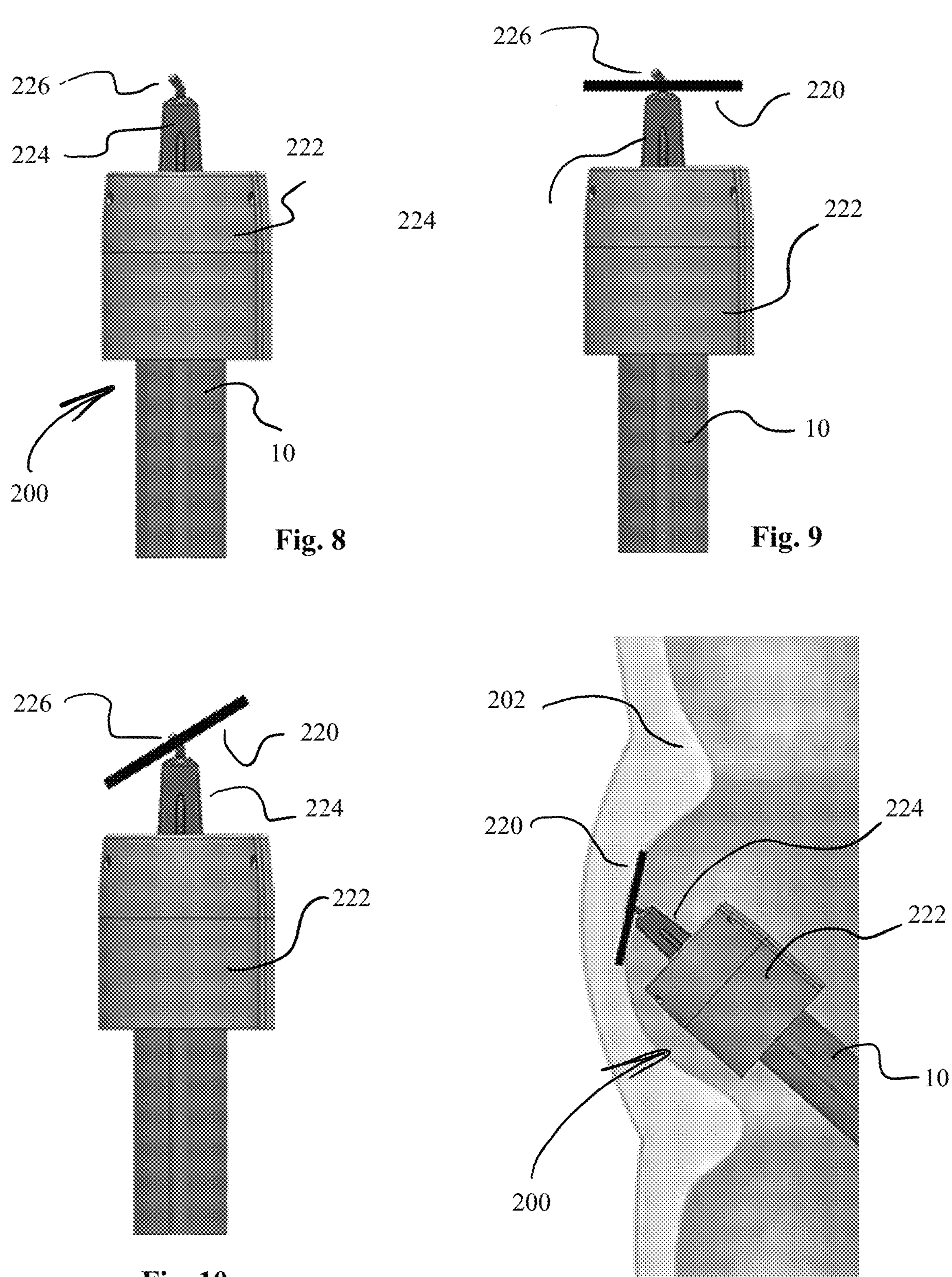
FIG. 8 is a side view of an alternate embodiment of the delivery system of the present invention for deployment of an endoscopic clip at an angled orientation.
FIG. 9 is a view similar to FIG. 8 showing one embodiment of a clip held in the jaws of the delivery instrument perpendicular to the longitudinal axis of the cap.
FIG. 10 is a view similar to FIG. 9 showing the clip held at an angle to the longitudinal axis of the cap.
FIG. 11 illustrates an endoscope delivering the system of FIG. 10 into the body lumen and placing the angled clip in abutment with the wall.

FIGS. 8-11 show an alternate clip delivery system 200. The cap 222 is connected to the endoscope 10. The system has two jaws 224, which can be similar to jaws 24*a*, 24*b*, but each has an angled pin 226 at its distal end for engagement with a clip, e.g., clip 220, as shown. Alternatively, only a portion of the pin 226 could be angled. The pins 226 of both jaws 224 are angled in the same direction. Only one jaw 224 is seen due to the side view of the system 200 in the FIGS. 8-11. (In a cross-sectional view at a 90 degree differing orientation, the jaw pins would angle outwardly as shown in FIG. 7). The system 200 allows for change in orientation of the clip 220 from a position perpendicular to the longitudinal axis of the cap 222 (FIG. 9) to a position angled with respect to the longitudinal axis of the cap 222 (FIG. 10). The change in the clip orientation could be achieved by preloading the clip in this orientation or by pressing the system 200 against a wall of a body lumen 202. This change in the clip orientation is particularly beneficial when the anatomical size of the target site (e.g., smaller anatomical structures) limits the scope's ability to articulate. (The clip can be angled at 90 degrees or at an acute angle). FIG. 11 shows the scope 10 delivering the system 200 into the body lumen 202 and placing the clip 220 in abutment with the wall. Note, in this embodiment, the clip 220 pivots so there is no need to bend the scope to a 90 degree or other angle which is beneficial due to the limited anatomical cross-section during insertion through the esophagus, colon, or other body lumen. Note, in some embodiments, when the jaws are in the closed position, there is little or no tension on the clip so it sits loosely on the pins, and once the clinician starts opening the clip (via opening of the jaws) the clip 220 will self-align with the angled pin 226 due to the clip spring force (FIG. 10).

In the systems disclosed herein, in some embodiments, the clip can sit loosely on the pins and a slight movement of jaws starts to tension the clip to secure it to the jaws.

Figures 12, 13, 13A, 14:
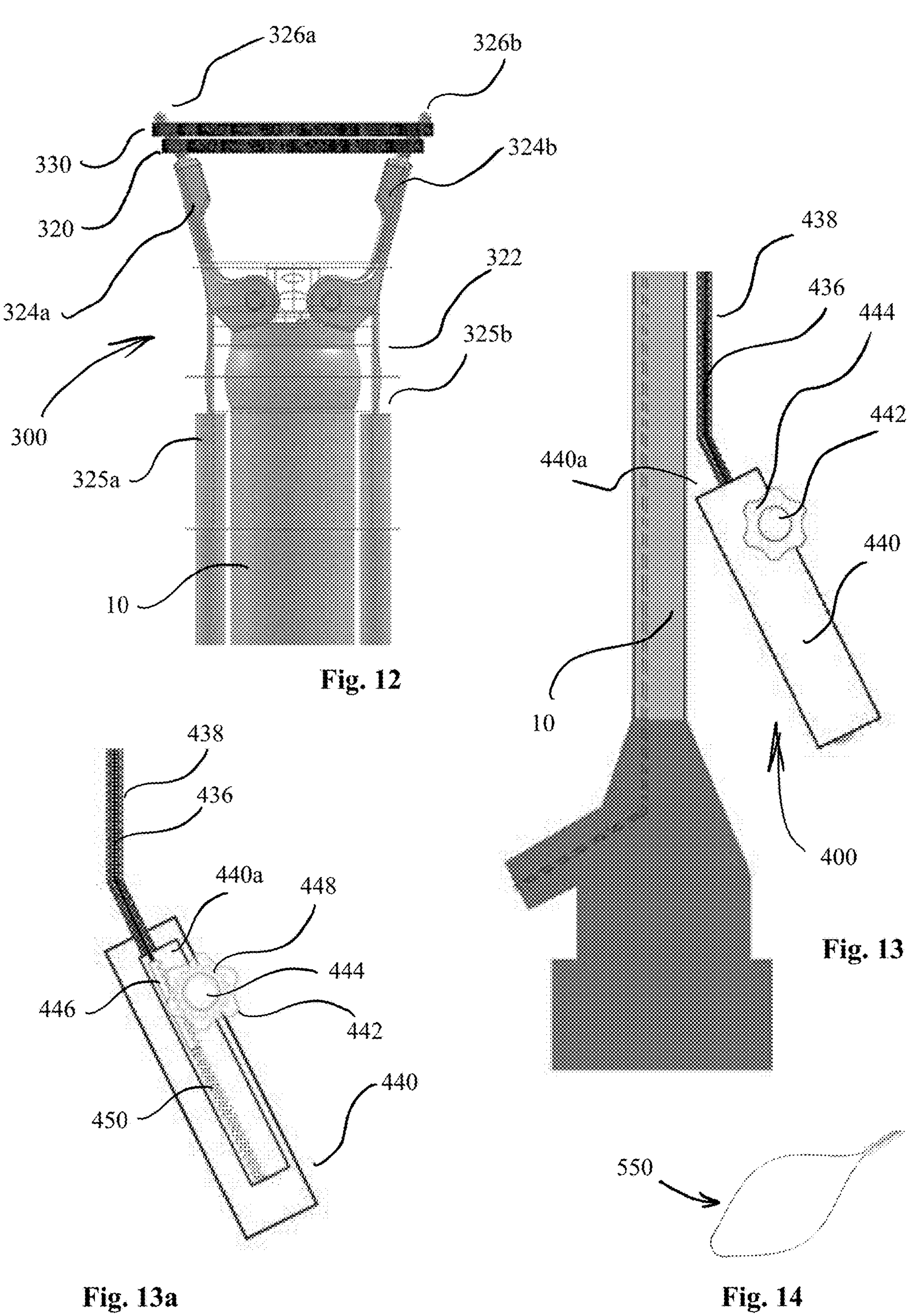
FIG. 12 is a side view of an alternate embodiment of a delivery system for deployment of two endoscopic clips simultaneously.
FIG. 13 is a side view of one embodiment of a control handle for actuating the cables of the delivery systems of the present invention.
FIG. 13*a* is a side view of a rack and pinon mechanism within the control handle of FIG. 13.
FIG. 14 is a top view of an endoscopic snare that could be used for tissue cutting in conjunction with the clip in clip-guided resection or other procedures.

FIG. 12 shows an alternate embodiment of a clip delivery system, designated by reference numeral 300, that is capable of delivering two clips 320 and 330 simultaneously. Use of two clips increases the closure and the retention forces. An alternative application of two clips is also described below. The system 300 is placed over endoscope 10 and includes a cap 322 and two jaws 324*a* and 324*b* pivoted via control cables 325*a*, 325*b* in a similar manner as cables 36*a*, 36*b* of FIG. 5. The jaws 324*a*, 324*b* could alternatively be pivoted in the other ways disclosed herein, e.g., one jaw pivots the other jaw via gears, cams, etc. The clip engagement members (pins) 326*a* and 326*b* preferably have an increased length compared to the foregoing embodiments, and are configured to engage with two clips simultaneously. One advantage of the two clips is a more secure closure of the defect and increased retention force on tissue. In alternative embodiments, another advantage is to facilitate placement of a snare and cutting tissue in the space between the two clips. Yet, another advantage is that clips of different properties, e.g., different compression forces, and/or different configurations and/or different functions can be utilized. For example, the first/primary clip, which is the closest to the closure site/tissue that is being preserved, is optimized for the tissue compression force/retention to assure secure closer of the defect. Such compression force could preferably be optimized to promote quick tissue healing, maintain blood perfusion in the compressed tissue and avoid undesirable/excessive tissue necrosis. In the multi-clip applications, the primary clip is located between the closure site/tissue that is being preserved and the second/secondary clip. In some embodiments, the secondary clip serves as a guiding member for a cutting instrument, for example, a snare. In such embodiments, the clip could have a different/lower compression/retention characteristics, as its primary function is not tissue closure. In an alternative embodiment, a primary clip can be placed on the healthy side for good compression and healing while a secondary clip can be placed on the target tissue which has an intentionally strong compression force to cause partial or complete necrosis of tissue that is targeted for removal/resection. If a strong enough compression force is applied, in some applications, the necrosis can cause tissue separation/sloughing off so that a cutting device does not need to be utilized to resect/dissect the unhealthy tissue. This can be beneficial where tissue cutting by a cutting instrument is challenging, for example due to anatomical limitations. In another example, one clip can have minimal compression force and act principally as a spacer.

FIG. 13 illustrates one embodiment of a control handle 400 which can be utilized in the clip deployment systems described herein. The control handle 400 is preferably configured for single handed operation by a user and controls the push-pull cable(s) described above. More specifically, a control cable 436 connects the jaws on the distal end of the clip deployment system to the control handle 440. The cable 436 is attached within the handle 440 and extends inside of conduit 438 (which can be similar to conduit 38*b*) of the cap. The control handle 400 can have an internal rack and pinion mechanism 446 and 448 that is located within the handle cover 440. The cable 436 is connected to the rack portion 446 of the mechanism, while a knob 442 connects to the pinion 448. A clinician can operate the distal jaws by pushing or pulling the cable 436 by rotating the control member, e.g., knob 442. This allows the user to open and close the clip gradually. The rack and pinion mechanism is preferably designed such that the force of the clip cannot move the jaws even if the user does not hold the knob 442. Optionally, the control handle 400 could have a frictional mechanism between the handle cover 440 and the knob 442 to prevent uncontrolled movement of the rack without the user input. Other mechanisms for this gradual position—retention controlled clip closure and/or opening are also contemplated.

The knob 442 could optionally be equipped with a rack 446 and a pinion 448 disengagement mechanism 444 as shown in FIG. 13*a*. When the mechanism 444 is activated, e.g., pulled laterally with respect to the cover 440 (transverse to a longitudinal axis of the rack 446) e.g., manually by the user, the pinion 448 moves laterally from the rack 446 and disengages from it (the planes no longer intersect). Therefore, the rack 446 is free to move forward under the force of the opened clip 20. The clip will begin closing pulling on the jaws that will pull on the cable, which will in turn pull on the rack. This will allow the user to close the clip more quickly rather than the gradual or incremental movement of the rack and pinion engagement. Optionally, the control handle 400 can have a spring 450 that pushes the pinion forward towards the distal end 440*a* of the handle cover 440 when the rack and pinion mechanism is disengaged. This pushes the cable 436 forward and closes the distal jaws facilitating a quicker closure of the clip. Alternative mechanisms of the control handle 400 are also contemplated. Note even in this "uncontrolled" closure, the delivery device preferably remains engaged with the clip so the user can still visually confirm placement and reposition the clip if necessary.

The rack disengagement mechanism in some embodiments can be selectively actuated by the clinician. In this manner, the controlled slower clip closure can be released to enable quicker closure of the clip. For example, the clip can be controllably closed for a portion of its closure and then released for more accelerated closure by disengagement of the rack and pinion if desired during the procedure.

Note instead of a cable, an elongated rod or other elongated member could be utilized with the various systems disclosed herein to pivot the jaw(s).

FIG. 14 shows a distal end of one form of an endoscopic snare 550, also shown on FIGS. 15-18, that could be used for tissue cutting in conjunction with the clip in the clip-guided resection procedures by way of example. This could also be used in other procedures. FIGS. 25-27 show alternative snare configurations and are described below.

Figures 15A, 15B, 15C, 16A, 16B, 17A, 17B, 18A, 18B:
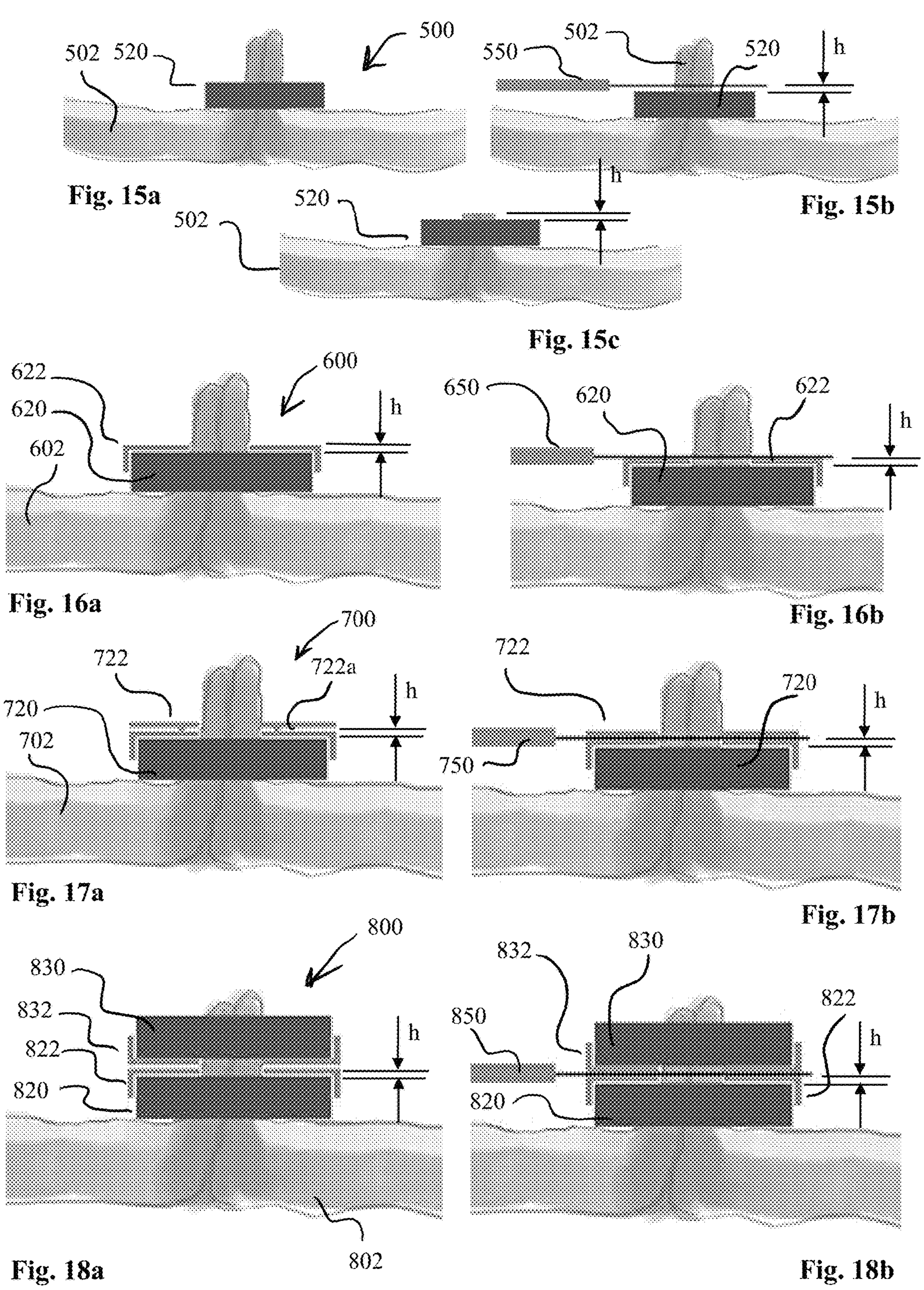
FIG. 15*a* illustrates a clip deployed over target tissue.
FIG. 15*b* illustrates a snare deployed over target tissue keeping a distance "h" between the clip of FIG. 15*a* and the snare.
FIG. 15*c* illustrates the tissue cut a distance "h" above the clip.
FIG. 16*a* illustrates an alternate embodiment of the clip having a spacer over the clip.
FIG. 16*b* illustrates a snare positioned over the spacer of FIG. 16*a;*
FIG. 17*a* illustrates an alternate embodiment of the clip 720 having a slotted spacer over the clip.
FIG. 17*b* illustrates a snare positioned in the slot of the spacer of FIG. 17*a;*
FIG. 18*a* illustrates the use of two clips with two spacers between the clips.
FIG. 18B illustrates a snare positioned between the two spacers of FIG. 18*a;*

FIGS. 15*a*-18*b* illustrate clip-guided resection procedures using various clip arrangements. FIG. 15*a* shows clip-guided resection using a clip 520, which is similar to the clip 20 described above. The clip 520 is deployed over a target tissue 502 (FIG. 15*a*). A snare 550 is deployed over the target tissue 502 preferably keeping a distance "h" between the clip 520 and the snare 550 (FIG. 15*b*). The snare 550 (and the other snares described herein or currently marketed snares) could cut tissue "cold" without use of energy of an external electrosurgical generator (not shown) or "hot" using an external electrosurgical generator. FIG. 15*c* shows the tissue 502 cut a distance "h" above the clip 520, which improves the retention force of the clip over the tissue and increases tissue burst pressure at the site of resection.

FIG. 16*a* shows an alternative arrangement wherein clip 620 has a spacer 622 that is placed over it or attached to it. The spacer helps maintain the desired distance between the snare and the clip. The spacer 622 provides a guiding member and has a thickness "h" that assures that when the tissue 602 is cut using a snare 650 (FIG. 16*b*), the tissue 602 is cut at a distance "h" above the clip 620. The spacer 622 could be made out of an electrical insulation material so that when a "hot" tissue cutting is performed the clip and the snare are electrically insulated from each other.

FIG. 17*a* shows an alternative arrangement wherein clip 720 that has a spacer 722 that is placed over it or attached to it. This could be in manufacture or by a clinician before use. The spacer 722 in this embodiment has slot 722*a* formed therein that is located at a distance "h" from the clip 720 and is configured and dimensioned to receive a snare. A snare 750 uses the slot 722*a* as a cutting guide that assures that the tissue 702 is cut at a distance "h" above the clip 720 (FIG. 17*b*).

FIG. 18*a* shows the use of two clips—clip 820 with a spacer 822 and clip 830 with a spacer 832. The clips are placed over the target tissue 802 such that the spacers 822, 832 are forming a gap between them. A snare 850 cuts the tissue using the gap between the spacers 822, 832 as a guide at a distance "h" from the clip 820 (FIG. 18*b*). The clip 830 and the spacer 832 are removed with the resected tissue.

Note the spacers of FIGS. 15*a*-18*a* can be used with any of the clip configurations disclosed herein or in the 2020/0397445 publication. Also, the snares of FIG. 15*a*-18*b* could be the snares of FIG. 14, 25 or 27, or other snare configurations can be implemented "hot" (with energy) or "cold" (without energy).

Figures 19A, 19B, 20, 21, 22, 23:
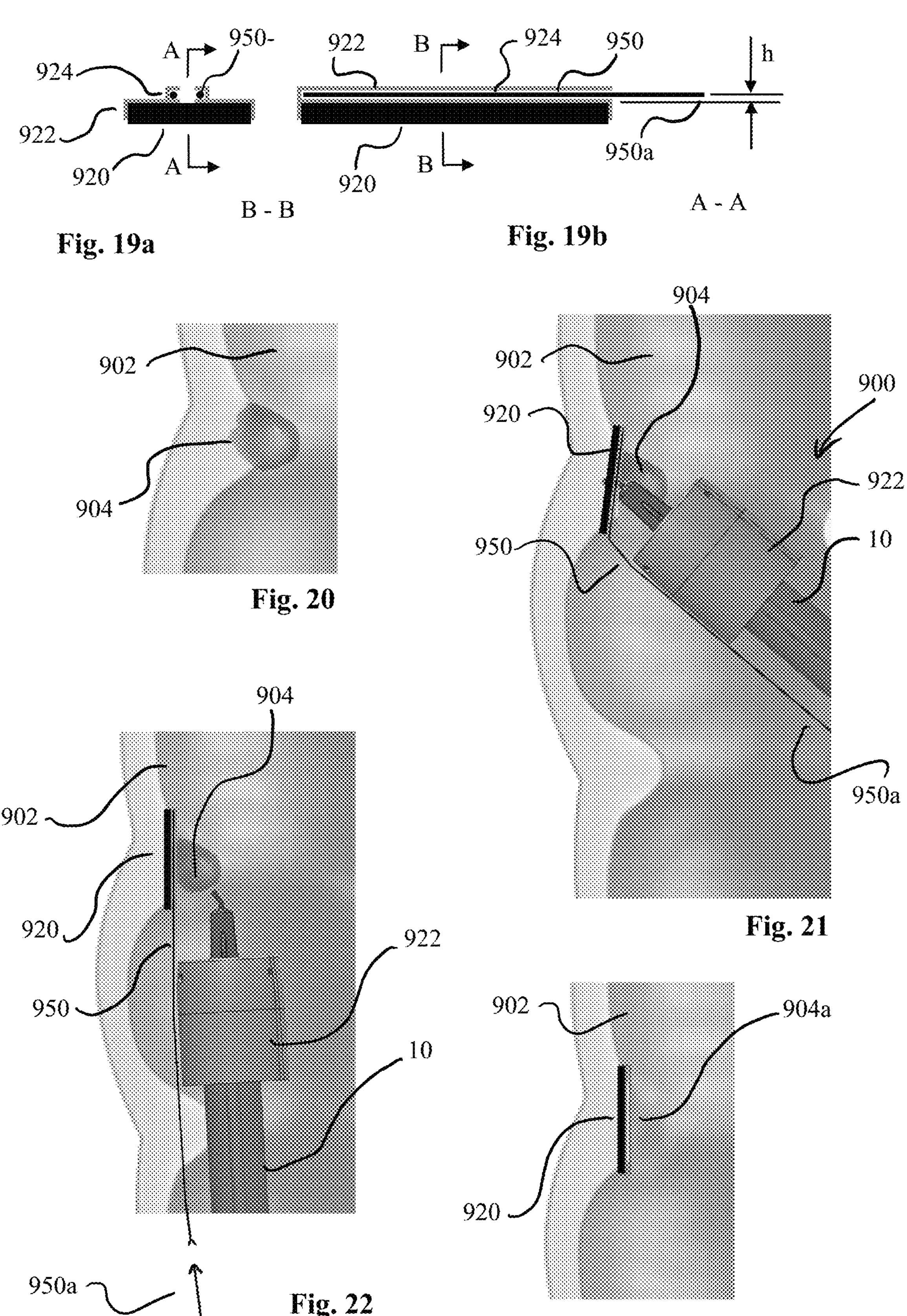
FIG. 19*a* illustrates an alternative embodiment of a clip having a spacer.
FIG. 19*b* illustrates a snare positioned in a slot in the spacer of FIG. 19*a;*
FIG. 20 illustrates an example of a target tissue, such as an adenoma/polyp or cancerous lesion, located inside of a body lumen.
FIG. 21 is a side view of an embodiment of the clip delivery system inserted over an endoscope into the body lumen until it reaches the target tissue.
FIG. 22 illustrates a snare engaging the tissue on a side of the clip of FIG. 21.
FIG. 23 illustrates the clip remaining on the tissue after withdrawal of the snare and delivery system of FIG. 22.

FIGS. 19*a* and 19*b* illustrate an alternative embodiment of a clip 920. The clip 920 has a spacer 922 that allows the clip 920 to be integrated/assembled with a tissue cutting/resection device, such as a snare 950. The snare 950 is located within a slot 924 of the spacer 922, such that it is located at a distance "h" from the clip 920. The proximal end 950*a* of the snare 950 extends to the proximal end of the scope such that a user could pull on it. When a user pulls on the proximal end 950*a*, the snare 950 slides out of the slot 924 and resects the target tissue.

Note snares 650, 750, 850 and 950 can be the same configuration as snare 550 of FIG. 14, or snare 1100 of FIG. 25, or other configurations. The snares can be configured with improved lateral stability.

FIGS. 20-23 illustrate an example of a clinical application of a clip delivery system for delivery clip 920 of FIG. 19*b*. FIG. 20 shows an example of a target tissue 904, such as an adenoma/polyp or cancerous lesion, located inside of a body lumen/cavity 902, such as a colon, stomach, esophagus, etc. A clip delivery system 900, which can be in the form of the clip delivery systems discussed above, is placed over the scope 10 and inserted into the body lumen/cavity 902 over the scope until it reaches the target tissue 904. The clip 920 is opened by the instrument jaws and closed for placement at the base portion of the lesion 904, such that the healthy wall of the body lumen/cavity 902 is on one side of the clip, while the lesion 904, which is targeted for resection, is on the opposite side of the clip 920. As a result, the clip 920 separates the healthy and diseased tissue. The delivery system 900 is then disengaged from the clip 920, i.e., the jaw pins are removed from the eyelets of the clip, leaving the clip 920 on the target tissue 904 with the snare extending therefrom, i.e., extending from the slot in the spacer 922.

(FIG. 22). The user can then pull on the proximal end 950*a* of the snare 950 to perform resection of the target tissue 904. Electrosurgical energy can in some embodiments be applied through the snare 950 to aid resection. Once the tissue 904 is resected, the system 900 along with the snare 950 and the resected tissue 904 are removed leaving the clip 920 attached to the body lumen/cavity 902 at the treatment site 904*a* (FIG. 23). Note the snare 950 can extend outside the cap 922 and scope 10 during insertion/delivery. Alternatively, the snare 950 could extend to the proximal end via the working channel of the scope.

FIG. 24 shows an alternative embodiment of a clip 1020 with an integrated tissue cutting/resection device 1050. Unlike the snare 950 that has the proximal end 950*a* that extends to the proximal end of the scope, the cutting/resection device 1050 is a loop that is integrated/assembled within a slot 1024 of the spacer 1022. The loop 1050 terminates at a proximal ring 1050*a* for a connection to a pulling device 1060, which is positioned inside of a conduit 1070. The pulling device 1060 could be introduced from the proximal end of the scope via the working channel and engaged with the proximal ring 1050*a* of the cutting snare/loop 1050. Alternatively, the pulling device 1060 could be inserted through a conduit of the cap (such as the caps discussed above) which is placed over or in abutment with the endoscope. After the clip 1020 is deployed (with the loop pre-attached/preloaded) similarly to how the clip 920 is deployed in FIG. 22, the user can pull on the device 1060 causing the cutting/resection device 1050 to resect the target issue. The cutting/resection device 1050 and the pulling device 1060 are then removed leaving the clip 1020 attached to the body lumen/cavity. If “hot” tissue cutting is preferred, energy could be transferred to the loop 1050 via the pulling device 1060 that is preferably an electric conductor using the conduit 1070, which is preferably made out of plastic, as an insulator.

An alternative embodiment of a cutting snare 1100 is shown in FIG. 25. The cutting snare 1100 has a cutting loop 1150 and structural elements 1152*a* and 1152*b* that are attached to the loop 1050 at the distal points 1150*a* and 1150*b*. The points 1150*a*, 1150*b* are spaced from the distal end of the loop creating two arcuate wires terminating proximally of the distalmost end of the snare. The snare 1100 is collapsible and resides inside of a conduit 1170. The snare 1100 could be delivered from the proximal end of the scope via the working channel. The snare could alternatively be delivered through an external channel of the cap.

The cutting snare 1100 could be used in conjunction with a clip 1120 as shown for example in FIG. 26. Clip 1120 can be similar to the clip 620 described above, or similar to other clips disclosed herein. When the clip 1120 is placed over the target tissue 1102, the structural elements 1152*a* and 1152*b* allow the user to apply a force F against the surface of a spacer 1122 facilitating use of the spacer 1122 as a cutting guide.

An alternative embodiment of a snare 1200 is illustrated in FIG. 27. A cutting element 1250 is supported by structural elements 1252*a* and 1252*b* at the points 1250*a* and 1250*b*. The snare 1200 could be used similarly to the snare 1100 described above.

Figures 28, 29, 30, 31:
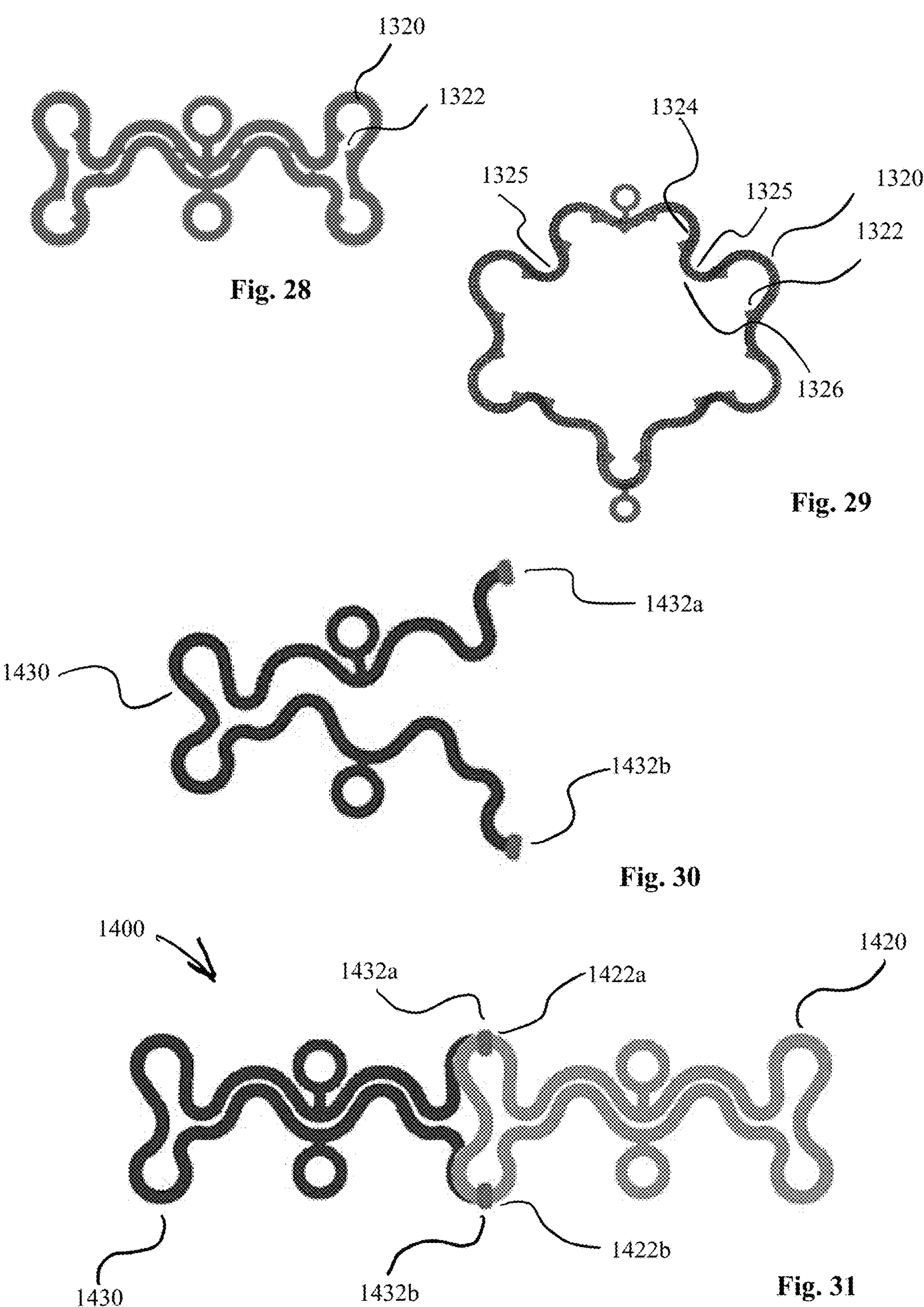
FIG. 28 is a top view of an alternate embodiment of a clip having tissue retention elements, the clip shown in the closed position.
FIG. 29 is a top view showing the clip of FIG. 28 in an open position.
FIG. 30 is a top view of an embodiment of a clip extension.
FIG. 31 is a top view of the clip extension of FIG. 30 connected to the clip of FIG. 2, the clip and clip extension shown in the closed position.

An alternative embodiment of an endoscopic clip 1320 is illustrated in FIGS. 28 and 29. The clip 1320 is equipped with at least one tissue engaging feature/element 1322. The element 1322 is intended to increase a retention force of the clip 1320 when it is placed over the target tissue. The elements 1322 could be in the form of surface protrusions such as a sharp spike or teeth, although other configurations are also contemplated to engage, and preferably penetrate, tissue. In an alternative embodiment, surface protrusions could be blunt, for example non penetrating such as a bump that embeds into tissue instead of penetrating it. In preferred embodiments, the elements 1322 extend (face inwardly) from inner surfaces of the clip and are located in positions such that when the clip 1320 is opened, the spikes are shielded by the geometry of the clip to minimize their interaction with/damage to the target tissue while the tissue is being introduced into the clip's opening. This should eliminate/minimize any unnecessary tissue damage. As shown, the spikes are oriented away from the center of the clip and positioned inside the curves 1324, i.e., not at the peaks 1326, of the valleys 1325 which face toward the center of the clip 1320. For clarity, only a few of the elements 1322 are labeled in FIGS. 28 and 29. Such tissue engaging elements can be positioned on the other clips disclosed herein.

An alternative endoscopic closure system 1400 is illustrated in FIGS. 30-32. The system 1400 includes a clip 1420 and a clip extension (extender) 1430 to provide for a longer closure length for example if the defect that is targeted for closure cannot be closed by a single clip. The extension 1430 has an opening on one side and at least one clip connecting (attaching) elements such as elements 1432*a* and 1432*b* that connect the extension (extended) 1430 to the clip 1420 at the connection portions 1422*a* and 1422*b*. This extends the clip length. In some embodiments, the clip extension is normally opened/expanded/spread out on the side of the opening. As shown, these connection points 1422*a*, 1422*b* are on one side of the clip, spaced from the tissue engaging/compressing surfaces of the clip. The connection can be in the form of a hook, by way of example. Simultaneous use of a second clip extension on the opposite side of the clip 1420 is also contemplated. In some embodiments, additional extensions 1430 could be attached to the closed end of the extension 1430 itself. The system 1400 is intended for closure of larger defects than the clip 1420 and is capable of closing by itself. The clip 1420 and the extension 1430 could be introduced simultaneously, i.e., they are interconnected prior to their introduction. Alternatively, and preferably, they could be introduced sequentially and connected in situ. For example, the clip 1420 is placed over the target tissue first, then the extension 1430 is delivered to the target closure site and engaged/connected to the clip 1420 at connections 1432*a*, 1432*b*. The extension 1430 is then expanded relying on the clip 1420 for support of the engaging elements 1432*a* and 1432*b* (FIG. 32) and closed over the target tissue (FIG. 31). The extension 1430 can be expanded prior to, after or simultaneous with the expansion of clip 1420. Jaws can engage the eyelets of the clip extender 1430 and clip 1420 in the same manner as described above. The extender 1430 in some embodiments has the same geometry as the clip, but could alternatively have a different geometry. The extender can also have surface protrusions such as spikes.

In the embodiment of FIGS. 33 and 34, clip 1500 has two ends 1502, 1504 that are separable to create an open side. This enables tissue to be inserted laterally through the open side into the gap 1506 between the tissue engaging surfaces 1507, 1509. The ends 1502, 1504 have a latching mechanism 1505 that enables the ends 1502, 1504 to releasably connect and disconnect. Other mechanisms for enabling disconnecting and reconnecting the ends 1502 and 1504 are contemplated. FIG. 33 illustrates the clip in the latched/connected condition; FIG. 34 illustrates the clip 1500 in the unlatched/disconnected configuration. The clip 1500 (and all other clips described herein) could be opened/reopened and closed/reclosed by a user at/near the target tissue site. This allows the clip 1500 to be placed and removed from the target tissue multiple times, for example, for temporary tissue/lumen/vessel compression/closure during a surgical manipulation.

As discussed above, the clip is preferably designed to provide compressive forces on tissue between the opposing tissue engaging/contacting surfaces. Sufficient pressure closes around the tissue to avoid leakage and promotes healing. Too little pressure can cause unwanted leakage and may not promote healing. However, too much pressure could crush the tissue and cause necrosis. Therefore, the clips of the present invention optimize the balance of these two competing factors by optimizing the clip force/pressure to optimize tissue compression. Note compression force can be measured by the force required to open the clip.

Sometimes, the target tissue is thin. For example, a human colonic wall could be less than 1 mm thick in some areas. In several clip embodiments described above, a gap exists between the tissue compressing surfaces. If the target tissue thickness is equal or less than the size of such gap, the compressive force is equal to zero. If a clip is fabricated with a zero gap, but the clip material is still in a relaxed state, the compressive force between the tissue compressing surfaces of the clip is equal to zero. The clip 1530 of FIG. 35 is directed to address this limitation. The clip 1530 has a loading member 1532 and a cover (or cover portion), preferably composed of a plastic material, positioned therearound. The cover 1535 is shown surrounding a loading member 1532 placing it in tension, and therefore positioning the opposing inner surfaces 1534 and 1536 in abutment with each other and creating a compressive force between them. Therefore, the cover 1535 functions to create a pre-load as not only is there a zero gap between the tissue compression surfaces when the clip is in the closed position, but the tissue contacting surfaces contact and press against each other to apply a compression force.

The loading member 1532 could be connected/attached to the cover 1535 using a snap-feature 1537 as shown on the cross-sectional view on FIG. 36. Other ways of attachment are also contemplated. The upper surfaces 1534*a* and 1536*a* and the inner surfaces 1534 and 1536 form steps in the profile that result in increased retention when the clip 1530 is placed over the tissue 1538 as shown on FIG. 36*a*. The cover 1535 also creates a spacing "h" so the tissue is not cut against the loading member 1532 itself. Alternatively, the cover can be overmolded to the clip as shown on the cross-sectional view on FIG. 36*b*. In these embodiments, the inner surfaces 1534' and 1536' if cover 1535' become the tissue engaging/compressing surfaces since the inner surface 1532*a*' of the loading member 1532' does not directly "engage" or "contact" the tissue or does that just partially (as in FIG. 36).

Thus, the cover can provide one or both of the following functions: a) it closes the gap between the tissue contacting surfaces creating a preload (need sufficient load to promote healing); and b) creates a space for cutting tissue. In some embodiments, the cover is designed to contribute an additional force to a preload/compressive force. One way to create such preload is to stretch the clip a bit then attach the cover so the clip engaging surfaces apply a compressive force.

The cover can be placed entirely over the clip (fully covering the inner and outer surfaces as in FIG. 35 or can partially cover the clip as in FIG. 36 and FIG. 36*a*. The partial cover can be continuous and interrupted.

Note the cover can also be considered a cover portion since it is attached to the loading member and becomes part of the clip. Therefore, tissue contacting surfaces of the clip can either be on the inner loading member or on the cover (cover portion) of the clip depending on the aforedescribed embodiment. In some embodiments, the cover is made out of an electric insulating material thus insulating a metal clip from the flow of energy, for example radio-frequency energy, from a cutting snare.

In an alternate embodiment, the preload is created without the plastic piece but is created in the clip itself. The clip, which can be made of Nitinol, has compression surfaces which overlap (sideways) so they are not in the same plane. Thus, a preload is created. The resulting clip causes the tissue contacting surfaces to press against each other with a sufficient pressure for creating the optimal compression force on tissue even when the tissue is very thin.

Figure 37:
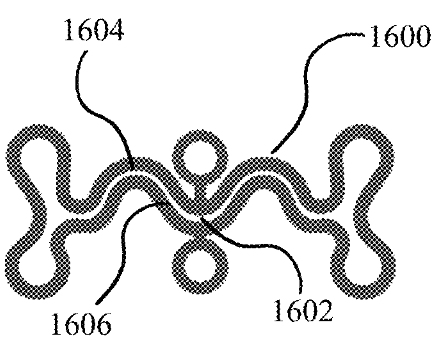
FIG. 37 is a top view of a clip having a gap between the tissue compressing surfaces in the closed position.
Figure 38:
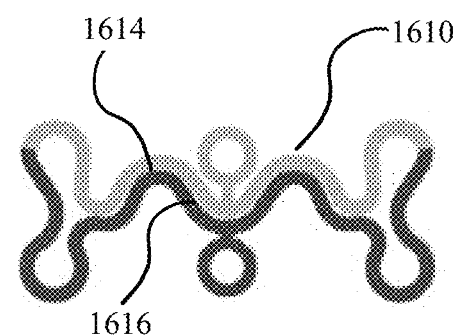
FIG. 38 is a top view of a clip having no gap between the tissue compressing surfaces in the closed position.
Figure 39A:
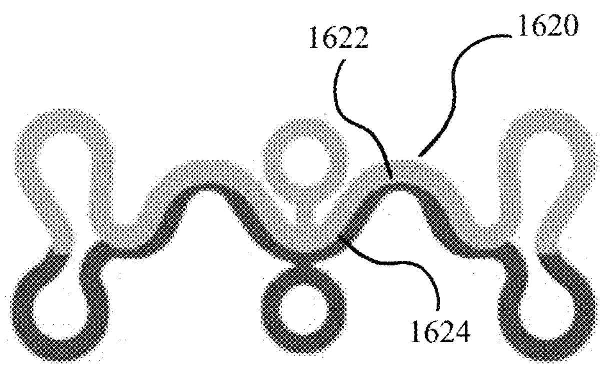
FIG. 39*a* is a top view of a clip having an overlap of the tissue compressing surfaces in the closed position.
Figure 39B:
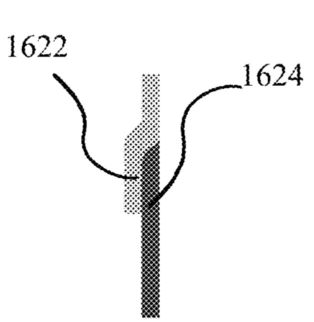
FIG. 39*b* is a side view of the clip of FIG. 39*a;*

FIGS. 37-39*b* illustrate the foregoing principles. In FIG. 37, the clip 1600 has a gap 1602 between the tissue contacting surfaces 1604, 1606 so does not apply a sufficient compressive force to tissue on thin tissue. In FIG. 38, the tissue contacting surfaces 1614, 1616 of the clip 1610 are in abutment, applying a greater compressive force than in FIG. 37 when the clip 1610 is placed over thin tissue. In FIGS. 39*a* and 39*b*, the tissue contacting surfaces 1622, 1624 of clip 1620 are not just in abutment as in FIG. 38, but overlap, e.g., are offset, providing a greater compressive force. (Note the clip is preferably a unitary structure and is shown in gray and black for clarity to depict the abutment and overlapping). One way to create this overlap is to have the clip deformed and heat treated such that the tissue contacting surfaces are in an overlapping position.

In some embodiments, the planarity of the clip could be restored while preserving the preload that is achieved during the deformation and heat treatment. This could be achieved if the first heat treating process is followed by a second heat treating process where the tissue contacting surfaces overlap each other in the other direction.

Figure 40A:
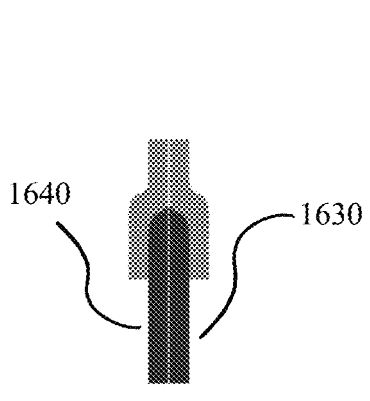
FIG. 40 is a side view of two overlapping clips positioned side by side.
FIG. 40*b* shows the two overlapping clips of FIG. 40*a* placed over tissue.
Figure 40B:
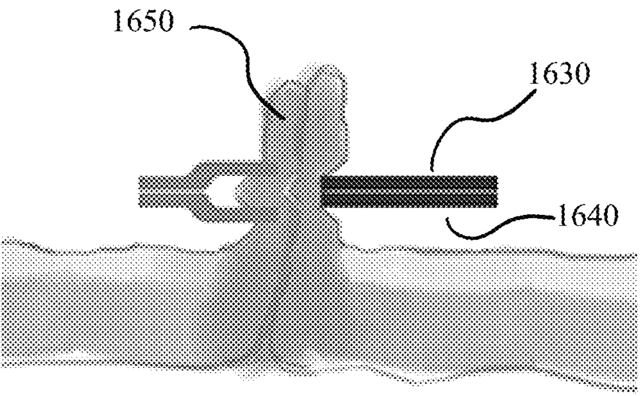

In FIGS. 40*a* and 40*b*, two overlapping clips 1630, 1640, each similar to clip 1620, are placed side by side. FIG. 40*b* depicts the two overlapping clips placed in tissue 1650. The present invention provides a clip having one or more of the foregoing feature(s), a clip deployment device (system) having or more of the foregoing features and/or a method utilizing the clip deployment devices and clips as disclosed herein.

The present invention also provides a system utilizing the clip deployment and the clip as disclosed herein. The clip deployment device can attach to an endoscope. The system of the present invention can also additionally include an endoscope over which the clip deployment device is mounted and/or one or more tissue grasping devices or other endoscopic instruments as described above for insertion through the clip deployment device and/or through the endoscope as described herein.

It should be appreciated that the discussion herein of the tissue contacting surfaces in abutment or overlapping relates to the clip in the fully closed position before applied to tissue. Once applied to tissue, the opposing tissue contacting (compressing) surfaces will not necessarily be in contact due to the interposing tissue, but will apply the optimized compression force on tissue as described herein.

Although the systems, devices, apparatus and methods of the subject invention have been described with respect to preferred embodiments, those skilled in the art will readily appreciate that changes and modifications may be made thereto without departing from the spirit and scope of the present invention as defined by the appended claims.

It will be understood that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure and it should be understood by those skilled in the art that various changes may be made (and equivalents may be substituted) without departing from the true spirit and scope of the present invention.

In addition, many modifications may be made to adopt a particular situation, material, composition of matter, process, process step or steps, to the objective spirit and scope of the present disclosure. All such modifications are intended to be within the scope of the claims appended hereto. For example, persons skilled in the art will understand that the elements and features shown or described in connection with one embodiment may be combined with those of another embodiment without departing from the scope of the present invention and will appreciate further features and advantages of the presently disclosed subject matter based on the description provided.

Where a range of values is provided, it is understood that each intervening value, between the upper and lower limit of that range and any other stated or intervening value in that stated range is encompassed by the present disclosure.

As used herein and in the appended claims, the singular forms “a”, “and”, and “the” include plural references unless the context clearly dictates otherwise.

Throughout the present disclosure, terms such as “approximately,” “generally,” “substantially,” and the like should be understood to allow for variations in any numerical range or concept with which they are associated. For example, it is intended that the use of terms such as “approximately”, “generally” and “substantially” should be understood to encompass variations on the order of 25% (e.g., to allow for manufacturing tolerances and/or deviations in design).

Although terms such as “first,” “second,” “third,” etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present invention.

Each and every claim is incorporated as further disclosure into the specification and represents embodiments of the present disclosure. Also, the phrases “at least one of A, B, and C” and “A and/or B and/or C” should each be interpreted to include only A, only B, only C, or any combination of A, B, and C.

Various combinations of all devices and methods described above may be utilized in the same procedure, sequentially and/or simultaneously.

What is claimed is:

1. A surgical clip for compressing body tissue comprising a first tissue compressing surface and a second tissue compressing surface, the clip having a closed position wherein the first and second tissue compressing surfaces are in contact with each other, wherein, in the closed position, the first and second tissue compressing surfaces comprise a non-linear surface and wherein the clip is equipped with at least one tissue engaging element in the form of a surface protrusion on the non-linear surface.

2. The surgical clip of claim 1, wherein in the closed position there is a compressive force between the first and second compressing surfaces.

3. The surgical clip of claim 1, wherein the clip is biased to a closed position.

4. The surgical clip of claim 1, wherein the clip is movable to a radially expanded open position wherein the first and second tissue compressing surfaces are spread away from each other.

5. The surgical clip of claim 1, wherein the clip is controllably movable from a closed position to an open position, wherein by moving the clip from the closed position to the open position, the clip both opens and deforms a geometry of the tissue compressing surfaces.

6. The surgical clip of claim 1, wherein the clip has a first receiving portion on a first side of the clip and a second receiving portion on a second side of the clip, the first tissue compressing surface being on the first side and the second tissue compressing surface being on the second side, the first receiving portion configured to receive a first clip engaging member and the second receiving portion configured to receive a second clip engaging member for moving the clip between open and closed positions.

7. The surgical clip of claim 1, wherein a non-linear geometry of the tissue compressing surfaces is different in an open position and the closed position.

8. The surgical clip of claim 1, wherein the clip further comprises a cover portion thereover covering a least a portion of the clip, the cover portion providing a force on the clip.

9. The surgical clip of claim 1, wherein in the closed position the tissue compressing surfaces overlap.

10. The surgical clip of claim 1, wherein the surgical clip is mountable to an endoscope for delivery by an endoscope.

11. The surgical clip of claim 1, wherein when the clip is moved to an open position, the clip is deformed so the first and second tissue compressing surfaces change configuration.

12. The surgical clip of claim 1, wherein the clip has a plurality of loops formed on first and second sides of the clip connecting the first and second tissue compressing surfaces, wherein movement of the clip to an open position alters a size and radius of the loops.

13. The surgical clip of claim 1, further comprising a spacer attached to the clip, the spacer separating the clip from a tissue resecting device.

14. The surgical clip of claim 1, further comprising a clip extender having first and second opposing tissue compressing surfaces, the clip extender connected to the clip to increase a length of the tissue compressing surfaces.

15. The surgical clip of claim 14, further comprising a connection mechanism on one or both of the clip and clip extender for connecting the clip extender to the clip in situ.

16. The surgical clip of claim 1, wherein the clip has an inner surface facing tissue, and a plurality of tissue retention members, the plurality of retention members facing inwardly from the inner surface.

17. The surgical clip of claim 16, wherein when the clip is moved to an open position, the tissue retention members are shielded by a geometry of the clip.

18. The surgical clip of claim 1, wherein the clip has a connection mechanism connecting two ends of the clip, the connection mechanism openable to spread apart the first and second tissue compressing surfaces on one side to create an open side and enable lateral receipt of tissue within the open side.

19. A surgical clip for compressing body tissue comprising a first tissue compressing surface and a second tissue compressing surface, the clip having a closed position, wherein the first and second tissue compressing surfaces are in contact with each other, and an open position, wherein the clip has a connection mechanism connecting two ends of the clip, the connection mechanism openable to spread apart the first and second tissue compressing surfaces on one side to create an open side and enable lateral receipt of tissue within the open side, and further comprising a spacer attached to the clip, the spacer separating the clip from a tissue resecting device.

20. A surgical clip for compressing body tissue comprising a first tissue compressing surface and a second tissue compressing surface, the clip having a closed and an open position, and a clip extender having first and second opposing tissue compressing surfaces, the clip extender connected to the clip to increase a length of the tissue compressing surfaces.

* * * * *